United States Patent
Wagner et al.

(10) Patent No.: US 10,233,436 B2
(45) Date of Patent: Mar. 19, 2019

(54) ADAMTS13-CONTAINING COMPOSITIONS HAVING THROMBOLYTIC ACTIVITY

(71) Applicants: Baxalta GmbH, Zug (CH); Baxalta Incorporated, Bannockburn, IL (US); Children's Medical Center Corporation, Boston, MA (US)

(72) Inventors: Denisa D. Wagner, Dover, MA (US); Anil Kumar Chauhan, Brookline, MA (US); Friedrich Scheiflinger, Vienna (AT); Barbara Plaimauer, Vienna (AT)

(73) Assignees: Baxalta Incorporated, Bannockburn, IL (US); Baxalta GmbH, Zug (CH); Children's Medical Center Corporation, Boston, MA (US)

( * ) Notice: Subject to any disclaimer, the term of this patent is extended or adjusted under 35 U.S.C. 154(b) by 987 days.

(21) Appl. No.: 13/747,307

(22) Filed: Jan. 22, 2013

(65) Prior Publication Data
US 2013/0136732 A1    May 30, 2013

Related U.S. Application Data

(62) Division of application No. 11/454,615, filed on Jun. 16, 2006, now abandoned.

(60) Provisional application No. 60/771,265, filed on Feb. 7, 2006, provisional application No. 60/729,323, filed on Oct. 21, 2005, provisional application No. 60/691,927, filed on Jun. 17, 2005.

(51) Int. Cl.
| | |
|---|---|
| *C12N 9/64* | (2006.01) |
| *A61K 38/17* | (2006.01) |
| *A61K 38/48* | (2006.01) |

(52) U.S. Cl.
CPC ............ *C12N 9/6489* (2013.01); *A61K 38/17* (2013.01); *A61K 38/4886* (2013.01)

(58) Field of Classification Search
None
See application file for complete search history.

(56) References Cited

U.S. PATENT DOCUMENTS

| | | | |
|---|---|---|---|
| 3,969,507 | A | 7/1976 | Kohri |
| 4,791,138 | A | 12/1988 | Schaub |
| 7,754,855 | B1 | 7/2010 | Cox, III et al. |
| 2003/0073116 | A1 | 4/2003 | Ginsburg et al. |
| 2004/0214346 | A1 | 10/2004 | Scheiflinger et al. |

FOREIGN PATENT DOCUMENTS

| | | |
|---|---|---|
| EP | 1391516 A1 | 2/2004 |
| EP | 1 568 782 A1 | 8/2005 |
| WO | WO 2002/042441 A2 | 5/2002 |
| WO | 2006/133955 A1 | 12/2006 |

OTHER PUBLICATIONS

Koster et al., Role of clotting factor VIII in effect of von willebrand factor on occurrence of deep-vein thrombosis, The Lancet, vol. 345, 1995, p. 152-55.*
Tsai et al, Coagulation factors, inflammation markers, and venous thromboembolism: the Longitudinal investigation of Thromboembolism Etiology (LITE), American Journal of Medicine, 2002, col. 113, p. 63-642. (Year: 2002).*
Egbrink et al.; "Fluid dynamics and the thromboembolic reaction in mesenteric arterioles and venules"; *Am. J. Physiol. Heart Circ. Physiol.*; 260:H1826-H1833 (1991).
Andre, P., et al.; *Blood*; "Platelets Adhere to and Translocate on von Willebrand Factor Presented by Endothelium in Stimulated Veins"; vol. 96:10; pp. 3322-3328 (2000).
Antoine, G., et al.; *British Journal of Haematology*: "ADAMTS13 Gene Defects in Two Brothers with Constitutional Thrombotic Thrombocytopenic Purpura and Normalization of von Willebrand Factor-Cleaving Protease Activity by Recombinant Human ADAMTS13"; vol. 120; pp. 821-824 (2003).
Arya, M., et al.; *Blood*; "Ultralarge Multimers of von Willebrand Factor Form Spontaneous High-Strength Bonds with the Platelet Glycoprotein 1b-IX Complex: Studies Using Optical Tweezers"; vol. 99:11; pp. 3971-3977 (2002).
Asada, Y., et al.; *Thrombosis Research*; "Immunohistochemistry of Vascular Lesion in Thrombotic Thrombocytopenic Purpura, with Special Reference to Factor VIII Related Antigen"; vol. 38:5; pp. 469-479 (1985).
Bagshewe, K.D., et al.; *Exp. Opin. Biol. Ther.*; "Antibody-directed enzyme prodrug therapy (ADEPT) for cancer," vol. 4, pp. 1777-1789 (2004).
Bergmeier, W., et al.; *Blood*; "Metalloproteinase Inhibitors Improve the Recovery and Hemostatis Function of in vitro-aged or -injured Mouse Platelets"; vol. 102:12; pp. 4229-4235 (2003).
Bergmeier, W., et al.; *Cytometry*: "Flow Cytometric Detection of Activated Mouse Integrin αIIbβ3 with a Novel Monoclonal Antibody"; vol. 48; pp. 80-86 (2002).
Bernardo, A., et al.; *Blood*; "Effects of Inflammatory Cytokines on the Release and Cleavage of the Endothelial Cell-Derived Ultralarge von Willebrand Factor Multimers Under Flow"; vol. 104:1; pp. 100-106 (2004).
Bruno, K., et al.; *Journal of Thrombosis and Haemostasis*; "Cloning, Expression and Functional Characterization of the Full-Length Murine ADAMTS-13"; vol. 3; pp. 1064-1073 (2005).
Chaitmain, B.R., et al.; *New Eng. J. Med.*; "A comparison between heparin and low-dose aspirin as adjunctive therapy with tissue plasminogen activator for acute myocardial infarction," Abstract, pp. 1-2 (1990).

(Continued)

*Primary Examiner* — Taeyoon Kim
*Assistant Examiner* — Tiffany M Gough
(74) *Attorney, Agent, or Firm* — Troutman Sanders LLP

(57) ABSTRACT

This invention relates to a pharmaceutical composition having thrombolytic activity comprising ADAMTS13, and to methods for treating or preventing a disorder associated with the formation and/or the presence of one or more thrombus and to methods of disintegrating one or more thrombus in a patient in need thereof. Furthermore, the invention relates to the use of a pharmaceutically effective amount of ADAMTS13 for the preparation of a pharmaceutical composition for treating or preventing a disorder associated with the formation or the presence of one or more thrombus and for disintegrating one or more thrombus in a patient in need thereof.

14 Claims, 9 Drawing Sheets

(56) References Cited

OTHER PUBLICATIONS

Crawley, J.T.B., et al.; *Blood*; "Proteolytic Inactivation of ADAMTS13 By Thrombin and Plasmin"; vol. 105:3; pp. 1085-1093 (2005).
Dent, J.A., et al.; *J. Clin. Invest.*; "Heterogeneity of Plasma von Willebrand Factor Multimers Resulting from Proteolysis of the Constituent Subunit"; vol. 88; pp. 774-782 (1991).
Dent, J.A., et al.; *Proc. Natl. Acad. Sci. USA*; "Identification of a Cleavage Site Directing the Immunochemical Detection of Molecular Abnormalities in Type IIA von Willebrand Factor"; vol. 87; pp. 6306-6310 (1990).
Dole, V.S., et al.; *Blood*; "Activated Platelets Induce Weibel-Palade-Body Secretion and Leukocyte Rolling in vivo: Role of P-Selectin"; vol. 106:7; pp. 2334-2339 (2005).
Dong, J-F, et al.; *Blood*; "ADAMTS-13 Rapidly Cleaves Newly Secreted Ultralarge von Willebrand Factor Multimers on the Endothelial Surface Under Flowing Conditions"; vol. 100:12; pp. 4033-4039 (2002).
Dong, J-F, et al.; *The Journal of Biological Chemistry*: "ADAMTS-13 Metalloprotease Interacts with the Endothelial Cell-Derived Ultra-Large von Willebrand Factor"; vol. 278:32; pp. 29633-29639 (2003).
Frenette, P.S., et al.; *Blood*, "Platelet-Endothelial Interactions in Inflamed Mesenteric Venules"; vol. 91:4; pp. 1318-1324 (1998).
Frenette, P.S., et al.; *Proc. Natl. Acad. Sci. USA*; "Platelets Roll on Stimulated Endothelium in vivo: An Interaction Mediated by Endothelial P-Selectin"; vol. 92; pp. 7450-7454 (1995).
Fujikawa, K., et al.; *Blood*; "Purification of Human von Willebrand Factor-Cleaving Protease and its Identification as a New Member of the Metalloproteinase Family"; vol. 98:6; pp. 1662-1666 (2001).
Furlan, M., et al.; *Bailliere's Clin. Haematology*; "Deficiency of von Willebrand Factor-Cleaving Protease in Familial and Acquired Thrombotic Thrombocytopenic Purpura"; vol. 11:2; pp. 509-514 (1998).
Furlan, M., et al.; *Blood*; "Acquired Deficiency of von Wiilebrand Factor-Cleaving Protease in a Patient with Thrombotic Thrombocytopenic Purpura"; vol. 91:8; pp. 2839-2846 (1998).
Furlan, M., et al.; *Blood*; "Deficient Activity of von Willebrand Factor-Cleaving Protease in Chronic Relapsing Thrombotic Thrombocytopenic Purpura"; vol. 89:9; pp. 3097-3103 (1997).
Furlan, M., et al.; *Blood*; "Partial Purification of a Characterization of a Protease From Human Plasma Cleaving von Willebrand Factor to Fragments Produced by in vivo Proteolysis"; vol. 87:10; pp. 4223-4234 (1996).
Furlan, M., et al.; *Proc. Natl. Acad. Sci. USA*; "Triplet Structure of von Willebrand Factor Reflects Proteolytic Degradation of High Molecular Weight Multimers"; vol. 90; pp. 7503-7507 (1993).
Furlan, M., et al.: *The New England Journal of Medicine*; "von Willebrand Factor-Cleaving Protease in Thrombotic Thrombocytopenic Purpura and the Hemolytic-Uremic Syndrome"; vol. 339:22: pp. 1578-1584 (1998).
Gerritsen, H.E., et al.; *Blood*; "Partial Amino Acid Sequence of Purified von Willebrand Factor-Cleaving Protease"; vol. 98:6; pp. 1654-1661 (2001).
Gerritsen, H.E., et al.; *Thromb Haemost*; "Assay of von Willebrand Factor (vWF)-Cleaving Protease Based on Decreased Collagen Binding Affinity of Degraded vWF"; vol. 82; pp. 1386-1389 (1999).
Gurfinkel, E.P., et al.; *JACC*; "Low molecular weight heparin versus regular heparin or aspirin in the treatment of unstable angina and silent ischemia," vol. 26, No. 2, pp. 313-318 (1995).
Hamilton, K.K., et al.; *J. Clin. Invest.*; "Changes in Cytosolic $Ca^{2+}$ Associated with von Willebrand Factor Release in Human Endothelial Cells Exposed to Histamine"; vol. 79; pp. 600-608 (1987).
Hodivala-Dilke, K.M., et al.: *J. Clin. Invest.*; "β3-Integrin-Deficient Mice are a Model for Glanzmann Thrombasthenia Showing Placental Defects and Reduced Survival"; vol. 103; pp. 229-238 (1999).
International Search Report for PCT/EP2006/005800 dated Oct. 4, 2006.

Klaus, C., et al.; *Blood*; "Epitope Mapping of ADAMTS13 Autoantibodies in Acquired Thrombotic Thrombocytopenic Purpura"; vol. 103:12; pp. 4514-4519 (2004).
Levy, G.G., et al.; *Nature*; "Mutations in a Member of the ADAMTS Gene Family Cause Thrombotic Thrombocytopenic Purpura"; vol. 413; pp. 488-494 (2001).
Moake, J.L, et al.; *The New England Journal of Medicine*; "Unusually Large Plasma Factor VIII :von Willebrand Factor Multimers in Chronic Relapsing Thrombotic Thrombocytopenic Purpura"; vol. 307:23; pp. 1432-1435 (1982).
Moake, J.L..; *Arch. Pathol. Lab. Med.*; "Thrombotic Thrombocytopenic Purpura and the Hemolytic Uremic Syndrome"; vol. 126; pp. 1430-1433 (2002).
Moake, J.L.; *Seminars in Hematology*; "von Willebrand Factor, ADAMTS-13, and Thrombotic Thrombocytopenic Purpura"; vol. 41:1; pp. 4-14 (2004).
Moake, J.L.; *The New England Journal of Medicine*; "Thrombotic Microangiopathies"; vol. 347:8; pp. 589-600 (2002).
Motto, D.G., et al.; *The Journal of Clinical Investigation*; "Shigatoxin Triggers Thrombotic Thrombocytopenic Purpura in Genetically Susceptible ADAMTS13-Deficient Mice"; vol. 115:10; pp. 2752-2761 (2005).
Ni, H., et al.; *The Journal of Clinical Investigation*; "Persistence of Platelet Thrombus Formation in Arterioles of Mice Lacking both von Willebrand Factor and Fibrinogen"; vol. 106:3; pp. 385-392 (2000).
Nishio, K., et. al.; *Proc. Natl. Acad. Sci. USA*; "Binding of Platelet Glycoprotein Ibα to von Willebrand Factor Domain A1 Stimulates the Cleavage of the Adjacent Domain A2 by ADAMTS13"; vol. 101:29; pp. 10578-10583 (2004).
Padilla, A., et al.; *Blood*; "P-Selectin Anchors Newly Released Ultralarge von Willebrand Factor Multimers to the Endothelial Cell Surface"; vol. 103:6; pp. 2150-2156 (2004).
Plaimauer, B., et al.; *Blood*; "Cloning, Expression, and Functional Characterization of the von Willebrand Factor-Cleaving Protease (ADAMTS13)"; vol. 100:10; pp. 3626-3632 (2002).
Reiter, R.A.,et al.; *Thromb Haemost*; "Changes in ADAMTS13 (von-Willebrand-Factor-Cieaving Protease) Activity after Induced Release of von Willebrand Factor During Acute Systemic Inflammation"; vol. 93; pp. 554-558 (2005).
Rieger, M.,et al.; *Thromb Haemost*; "Relation Between ADAMTS13 Activity and ADAMTS13 Antigen Levels in Healthy Donors and Patients with Thrombotic Microangiopathies"; vol. 95; pp. 1-9 (2006).
Ruggenenti, P., et al.; *Kidney International*; "Thrombotic Microangiopathy, Hemolytic Uremic Syndrome, and Thrombotic Thrombocytopenic Purpura"; vol. 60; pp. 831-846 (2001).
Ruggeri, Z.M.,et al.; *Blood*; "Contribution of Distinct Adhesive Interactions to Platelet Aggregation in Flowing Blood"; vol. 94:1; pp. 172-178 (1999).
Sadler, J.E., et al.; *Hematology*: "Recent Advances in Thrombotic Thrombocytopenic Purpura"; pp. 407-423 (2004).
Sadler, J.E.; *Annual Review of Medicine*; "New Concepts in von Willebrand Disease"; vol. 56; pp. 173-191 (2005).
Savage, B., et al.; *Cell*; "Specific Synergy of Multiple Substrate-Receptor Interactions in Platelet Thrombus Formation under Flow"; vol. 94; pp. 657-666 (1998).
Scheiflinger, F., et al.; *Blood*; "Nonneutralizing IgM and IgG Antibodies to von Willebrand Factor-Cleaving Protease (ADAMTS-13) in a Patient with Thrombotic Thrombocytopenic Purpura"; vol. 102:9; pp. 3241-3243 (2003).
Siedlecki, C.A., et al.; *Blood*; "Shear-Dependent Changes in the Three-Dimensional Structure of Human von Willebrand Factor"; vol. 88:8; pp. 2939-2950 (1996).
Slayter, H., et al.; *The Journal of Biological Chemistry*; "Native Conformation of Human von Willebrand Protein"; vol. 260:14; pp. 8559-8563 (1985).
Soejima, K., et al.; *Blood*; "ADAMTS-13 Cysteine-Rich/Spacer Domains are Functionally Essential for von Willebrand Factor Cleavage"; vol. 102:9; pp. 3232-3237 (2003).

(56) References Cited

OTHER PUBLICATIONS

Soejima, K., et al.; *Journal of Biochemistry*: "A Novel Human Metalloprotease Synthesized in the Liver and Secreted into the Blood: Possibly, the von Willebrand Factor-Cleaving Protease"; vol. 130:4; pp. 475-480 (2001).
Sporn, L.A., et al.; *Blood*; "von Willebrand Factor Released from Weibei-Palade Bodies Binds More Avidly to Extracellular Matrix than that Secreted Constitutively"; vol. 69:5; pp. 1531-1534 (1987).
Sporn, L.A., et al.; *Cell*; "Inducible Secretion of Large, Biologically Potent von Willebrand Factor Multimers"; vol. 46; pp. 185-190 (1986).
Tsai, H-M, et al.; *Biochemical and Biophysical Research Communications*; "Endothelial Cell-Derived High Molecular Weight von Willebrand Factor is Converted into the Plasma Multimer Pattern by Granulocyte Proteases"; vol. 158:3; pp. 980-985 (1989).
Tsai, H-M, et al.; *Blood*; "Multimeric Composition of Endothelial Cell-Derived von Willebrand Factor"; vol. 73:8; pp. 2074-2076 (1989).
Tsai, H-M, et al.; *Blood*; "Proteolytic Cleavage of Recombinant Type 2A von Willebrand Factor Mutants R834W and R834Q: Inhibition by Doxycyciine and by Monoclonal Antibody VP-1"; vol. 89:6; pp 1954-1962 (1997).
Tsai, H-M, et al.; *New England Journal of Medicine*; "Antibodies to von Willebrand Factor-Cleaving Protease in Acute Thrombotic Thrombocytopenic Purpura"; vol. 339:22; pp. 1585-1594 (1998).
Tsai, H-M; *Blood*; "Physiologic Cleavage of von Willebrand Factor by a Plasma Protease is Dependent on its Conformation and Requires Calcium Ion"; vol. 87:10; pp. 4235-4244 (1996).
Tsai, H-M; *Journal of Molecular Medicine*; "von Willebrand Factor, ADAMTS13, and Thrombotic Thrombocytopenic Purpura"; vol. 80; pp. 639-647 (2002).
Tsai, H-M; *Journal of Thrombosis and Haemostasis*; "Deficiency of ADAMTS-13 in Thrombotic and Thrombocytopenic Purpura"; pp. 2038-2047 (2003).
Uemura, M., et al.; *Blood*; First Edition Paper; "Localization of ADAMTS13 to the Stellate Cells of Human Liver"; pp. 1-13 (2005).
Wagner, D.D., et al.; *Mayo Clin Proc*; "von Willebrand Factor and the Endothelium"; vol. 66; pp. 621-627(1991).
Wagner D.D., et al.; *The Journal of Cell Biology*; "Immunolocalization of von Willebrand Protein in Weibel-Palade Bodies of Human Endothelial Cells"; vol. 95; pp. 355-350 (1982).
Zheng, X., et al.; *The Journal of Biological Chemistry*; "Structure of von Willebrand Factor-Cleaving Protease (ADAMTS13), a Metalloprotease Involved in Thrombotic Thrombocytopenic Purpura"; vol. 276:44; pp. 41059-41063 (2001).
Zhou, W., et al.; *Laboratory Investigation*; "ADAMTS13 is Expressed in Hepatic Stellate Cells"; vol. 85; pp. 780-788 (2005).
Zimmerman, T.S., et al.; *The Journal of Clinical Investigation*; "Subunit Composition of Plasma von Willebrand Factor"; vol. 77; pp. 947-951 (1986).
Bongers, Tamara N. et al., "High von Willebrand Factor Levels Increase the Risk of First Ischemic Stroke: Influence of ADAMTS13, Inflammation, and Genetic Variability", Stroke (2006), vol. 37, pp. 2672-2677.
Chauhan, Anil K. et al., "The Metalloprotease ADAMTS13 is a Natural Anti-Thrombotic", Blood (2005), vol. 106, Abstract 409, 1 page.
De Meyer, Simon F. et al., "Protective Anti-inflammatory Effect of ADAMTS13 on Myocardial Ischemia/reperfusion Injury in Mice", Blood (2012), vol. 120:26, pp. 5217-5223.
Kleinschnitz, Christoph et al., "Targeting Platelets in Acute Experimental Stroke: Impact of Glycoprotein Ib, VI, and IIb/IIIa Blockade on Infarct Size, Functional Outcome, and Intracranial Bleeding", Circulation (2007), vol. 115, pp. 2323-2330.
Kokame, K. et al., "FRETS-VWF73, a first fluorogenic substrate for ADAMTS13 assay", British Journal of Haematology (2005), 129:1, pp. 93-100.
Miyata, Toshiyuki et al., "Measurement of ADAMTS13 Activity and Inhibitors", Current Opinion in Hematology (2005), vol. 12, pp. 384-389.
Spiel, Alexander O. et al., Von Willebrand Factor in Cardiovascular Disease: Focus on Acute Coronary Syndromes, Circulation (2008), vol. 117, pp. 1449-1459.
Zhao, Bing-Qiao et al., "VWF-Cleaving Protease ADAMTS13 Reduces Brain Injury following Ischemic Stroke in Mice: Essential Role for VWF in Stroke", Blood (2008), vol. 112, abstract 259, 1 page.

\* cited by examiner

A. Infusion of WT mice with Polyclonal Anti-hu ADAMTS13 Ab mimics *Adamts13* -/- phenotype B. Platelet Strings anchor to endothelium for up to 10 seconds in WT infused with polyclonal Anti-hu ADAMTS13 Ab similar to Adamts 13-/- KO mice Polyclonal Anti-hu ADAMTS 13 induces thrombi in microvenules of WT mice after A23187 infusion

Figure 9

Table 1. Hemodynamic characteristics of A23187 activated venules

| Genotype | Venule Diameter (μm) | Centerline velocity (mm/s) | Shear rate ($s^{-1}$) |
| --- | --- | --- | --- |
| *Adamts13* WT (n=5) | 31.51 ±1.79 | 1.43 ±0.07 | 213 ±14.10 |
| *Adamts13* -/- (n=5) | 26.36 ±1.95 | 1.28 ±0.13 | 244 ±28.29 |

Table 2. Hemodynamic characteristics of $FeCl_3$ injured arterioles

| Genotype | Arteriole Diameter (μm) | Centerline velocity (mm/s) | Shear rate ($s^{-1}$) |
| --- | --- | --- | --- |
| *Adamts13* WT (n=12) | 103.91 ±9.29 | 33.33 ±1.72 | 1688.16 ±143.32 |
| *Adamts13* -/- (n=12) | 93.26 ±10.48 | 28.05 ±2.10 | 1646.83 ±157.16 |

ADAMTS13-CONTAINING COMPOSITIONS HAVING THROMBOLYTIC ACTIVITY

CROSS-REFERENCES TO RELATED APPLICATIONS

This application is a divisional application of U.S. patent application Ser. No. 11/454,615, filed Jun. 16, 2006, which claims benefit of U.S. Provisional Patent Application No. 60/691,927, filed Jun. 17, 2005; U.S. Patent Application No. 60/729,323, filed Oct. 21, 2005; and U.S. Application No. 60/771,265, filed Feb. 7, 2006; each of which applications is hereby incorporated by references in its entirety for all purposes.

FIELD OF THE INVENTION

This invention relates to pharmaceutical compositions having thrombolytic activity comprising a pharmaceutically effective amount of ADAMTS13, to methods of treating or preventing disorders associated with the formation and/or the presence of one or more thrombus as well as to methods for disintegrating one or more thrombus in a patient in need thereof. Furthermore, the invention relates to the use of a pharmaceutically effective amount of ADAMTS13 for the preparation of a pharmaceutical composition for treating or preventing a disorder associated with the formation and/or the presence of one or more thrombus and for disintegrating one or more thrombus in a patient in need thereof.

BACKGROUND OF THE INVENTION

Thrombotic thrombocytopenic purpura (TTP) is a disorder characterized by thrombotic microangiopathy, thrombocytopenia and microvascular thrombosis that can cause various degrees of tissue ischemia and infarction. Clinically, TTP patients are diagnosed by symptoms such as thrombocytopenia, schistocytes (fragments of erythrocytes) and elevated levels of lactate dehydrogenase (Moake J L. Thrombotic microangiopathies. *N Engl J. Med.* 2002; 347: 589-600; Moake J L. von Willebrand factor, ADAMTS-13, and thrombotic thrombocytopenic purpura. *Semin Hematol.* 2004; 41:4-14; Sadler J E, Moake J L, Miyata T, George J N. Recent advances in thrombotic thrombocytopenic purpura. *Hematology (Am Soc Hematol Educ Program).* 2004; 407-423; Sadler J E. New concepts in von Willebrand disease. *Annu Rev Med.* 2005; 56:173-191). In 1982, Moake et al. found unusually large von Willebrand factor (UL-vWF) multimers in the plasma of the patients with chronic relapsing TTP (Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. *N Engl J Med.* 1982; 307:1432-1435). The link between UL-vWF and TTP gained support with independent findings by Furlan et al. and Tsai and Lian that most patients suffering from TTP are deficient in a plasma metalloprotease that cleaves vWF (Furlan M, Robles R, Solenthaler M, Wassmer M, Sandoz P, Laemmle B. Deficient activity of von Willebrand factor-cleaving protease in chronic relapsing thrombotic thrombocytopenic purpura. *Blood.* 1997; 89:3097-3103; Tsai H M, Sussman, I I, Ginsburg D, Lankhof H, Sixma J J, Nagel R L. Proteolytic cleavage of recombinant type 2A von Willebrand factor mutants R834W and R834Q: inhibition by doxycycline and by monoclonal antibody VP-1. *Blood.* 1997; 89:1954-1962; Tsai H M, Lian E C. Antibodies to von Willebrand factor-cleaving protease in acute thrombotic thrombocytopenic purpura. *N Engl J. Med.* 1998; 339:1585-1594). The protease belongs to the ADAMTS family and is designated as ADAMTS13 (A Disintegrin-like And Metalloprotease with Thrombospondin type I repeats), a 190 kDa glycosylated protein produced predominantly by the liver (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. *Nature.* 2001; 413: 488-494; Fujikawa K, Suzuki H, McMullen B, Chung D. Purification of human von Willebrand factor-cleaving protease and its identification as a new member of the metalloproteinase family. *Blood.* 2001; 98:1662-1666; Zheng X, Chung D, Takayama T K, Majerus E M, Sadler J E, Fujikawa K. Structure of von Willebrand factor-cleaving protease (ADAMTS13), a metalloprotease involved in thrombotic thrombocytopenic purpura. *J Biol Chem.* 2001; 276:41059-41063; Soejima K, Mimura N, Hirashima M, Maeda H, Hamamoto T, Nakagaki T, Nozaki C. A novel human metalloprotease synthesized in the liver and secreted into the blood: possibly, the von Willebrand factor-cleaving protease? *J Biochem (Tokyo).* 2001; 130:475-480; Gerritsen H E, Robles R, Lammle B, Furlan M. Partial amino acid sequence of purified von Willebrand factor-cleaving protease. *Blood.* 2001; 98:1654-1661). Mutations in the ADAMTS13 gene have been shown to cause TTP (Levy G G, Nichols W C, Lian E C, Foroud T, McClintick J N, McGee B M, Yang A Y, Siemieniak D R, Stark K R, Gruppo R, Sarode R, Shurin S B, Chandrasekaran V, Stabler S P, Sabio H, Bouhassira E E, Upshaw J D, Jr., Ginsburg D, Tsai H M. Mutations in a member of the ADAMTS gene family cause thrombotic thrombocytopenic purpura. *Nature.* 2001; 413:488-494). Idiopathic TTP, often caused by autoantibodies inhibiting ADAMTS-13 activity, is a more common disorder that occurs in adults and older children and can recur at regular intervals in 11-36% of patients (Tsai H M, Lian E C. Antibodies to von Willebrand factor-cleaving protease in acute thrombotic thrombocytopenic purpura. *N Engl J. Med.* 1998; 339:1585-1594; Furlan M, Lammle B. Deficiency of von Willebrand factor-cleaving protease in familial and acquired thrombotic thrombocytopenic purpura. *Baillieres Clin Haematol.* 1998; 11:509-514). Non neutralizing autoantibodies could also inhibit ADAMTS activity by inducing clearance from circulation (Scheiflinger F, Knobl P, Trattner B, Plaimauer B, Mohr G, Dockal M, Dorner F, Rieger M. Nonneutralizing IgM and IgG antibodies to von Willebrand factor-cleaving protease (ADAMTS-13) in a patient with thrombotic thrombocytopenic purpura. *Blood.* 2003; 102:3241-3243). Plasma ADAMTS13 activity in healthy adults ranges from 50% to 178% (Moake J L. Thrombotic thrombocytopenic purpura and the hemolytic uremic syndrome. *Arch Pathol Lab Med.* 2002; 126:1430-1433). In most patients with familial or acquired TTP, plasma ADAMTS13 activity is absent or less than 5% of the normal. Without treatment the mortality rate exceeds 90%, but plasma therapy has reduced mortality to about 20% (Moake J L. Thrombotic thrombocytopenic purpura and the hemolytic uremic syndrome. *Arch Pathol Lab Med.* 2002; 126:1430-1433).

vWF synthesized in megakaryocytes and endothelial cells is stored in platelet α-granules and Weibel-Palade bodies, respectively, as ultra large vWF (UL-vWF) 5. Moake J L, Rudy C K, Troll J H, Weinstein M J, Colannino N M, Azocar J, Seder R H, Hong S L, Deykin D. Unusually large plasma factor VIII:von Willebrand factor multimers in chronic relapsing thrombotic thrombocytopenic purpura. *N Engl J Med.* 1982; 307:1432-1435; Wagner D D, Olmsted J B, Marder V J. Immunolocalization of von Willebrand protein in Weibel-Palade bodies of human endothelial cells. *J Cell Biol.* 1982; 95:355-360; Wagner D D, Bonfanti R. von Willebrand factor and the endothelium. *Mayo Clin Proc.* 1991; 66:621-627; Sporn L A, Marder V J, Wagner D D. von Willebrand factor released from Weibel-Palade bodies binds more avidly to extracellular matrix than that secreted constitutively. *Blood.* 1987; 69:1531-1534; Tsai H M, Nagel R L, Hatcher V B, Sussman, I I. Endothelial cell-derived high molecular weight von Willebrand factor is converted into the plasma multimer pattern by granulocyte proteases. *Biochem Biophys Res Commun.* 1989; 158:980-985; Tsai H M, Nagel R L, Hatcher V B, Sussman, I I. Multimeric composition of endothelial cell-derived von Willebrand factor. *Blood.* 1989; 73:2074-2076). Once secreted from endothelial cells, these UL-vWF multimers are cleaved by ADAMTS13 in circulation into a series of smaller multimers at specific cleavage sites within the vWF molecule (Tsai H M, Nagel R L, Hatcher V B, Sussman, I I. Endothelial cell-derived high molecular weight von Willebrand factor is converted into the plasma multimer pattern by granulocyte proteases. *Biochem Biophys Res Commun.* 1989; 158:980-985; Dent J A, Galbusera M, Ruggeri Z M. Heterogeneity of plasma von Willebrand factor multimers resulting from proteolysis of the constituent subunit. *J Clin Invest.* 1991; 88:774-782; Furlan M, Robles R, Affolter D, Meyer D, Baillod P, Lammle B. Triplet structure of von Willebrand factor reflects proteolytic degradation of high molecular weight multimers. *Proc Natl Acad Sci USA.* 1993; 90:7503-7507). The protease cleaves at the Tyr842-Met843 bond in the central A2 domain of the mature vWF subunit and requires zinc or calcium for activity (Dent J A, Berkowitz S D, Ware J, Kasper C K, Ruggeri Z M. Identification of a cleavage site directing the immunochemical detection of molecular abnormalities in type IIA von Willebrand factor. *Proc Natl Acad Sci USA.* 1990; 87:6306-6310). vWF exists in "ball-of-yarn" and filamentous form as seen by electron microscopy (Slayter H, Loscalzo J, Bockenstedt P, Handin R I. Native conformation of human von Willebrand protein. Analysis by electron microscopy and quasi-elastic light scattering. *J Biol Chem.* 1985; 260:8559-8563). Furthermore, atomic force microscopy confirms that vWF exits in a globular conformation under static conditions and an unfolded filamentous state after exposure to shear stress (Siedlecki C A, Lestini B J, Kottke-Marchant K K, Eppell S J, Wilson D L, Marchant R E. Shear-dependent changes in the three-dimensional structure of human von Willebrand factor. *Blood.* 1996; 88:2939-2950). This could occur also in vivo when one end of the vWF filament is anchored to a surface.

UL-vWF multimers, present in Weibel-Palade bodies, when released by activated endothelial cells bind platelets more tightly (through GPIbα) than plasma vWF (27. Arya M, Anvari B, Romo G M, Cruz M A, Dong J F, McIntire L V, Moake J L, Lopez J A. Ultralarge multimers of von Willebrand factor form spontaneous high-strength bonds with the platelet glycoprotein Ib-IX complex: studies using optical tweezers. *Blood.* 2002; 99:3971-397). It was demonstrated in vitro that the platelets align as beads on the released UL-vWF on the endothelial surface (Dong J F, Moake J L, Nolasco L, Bernardo A, Arceneaux W, Shrimpton C N, Schade A J, McIntire L V, Fujikawa K, Lopez J A. ADAMTS-13 rapidly cleaves newly secreted ultralarge von Willebrand factor multimers on the endothelial surface under flowing conditions. *Blood.* 2002; 100:4033-4039).

These UL-vWF secreted multimers are anchored to the cell surface as long stringlike structures. These multimers are then cleaved by ADAMTS13 as they are secreted from stimulated endothelial cells (Dong J F, Moake J L, Bernardo A, Fujikawa K, Ball C, Nolasco L, Lopez J A, Cruz M A. ADAMTS-13 metalloprotease interacts with the endothelial cell-derived ultra-large von Willebrand factor. *J Biol Chem.* 2003; 278:29633-29639).

Thrombi of TTP patients consist of little fibrin and mainly of vWF and platelets, suggesting vWF-mediated platelet aggregation as a cause of thrombosis (30. Asada Y, Sumiyoshi A, Hayashi T, Suzumiya J, Kaketani K. Immunohistochemistry of vascular lesion in thrombotic thrombocytopenic purpura, with special reference to factor VIII related antigen. *Thromb Res.* 1985; 38:469-479). Patients with relapsing TTP have ultra-large multimers in the plasma. The UL-vWF multimers accumulate over time because the persistence of the inhibitor (Anti-ADAMTS13 Ab) decreases ADAMTS13 activity. The UL-vWF multimers are hyperactive and unfold as a result of shear stress causing platelet aggregation, resulting in intravascular thrombosis (Tsai H M. Von Willebrand factor, ADAMTS13, and thrombotic thrombocytopenic purpura. *J Mol Med.* 2002; 80:639-647; Tsai H M. Deficiency of ADAMTS-13 in thrombotic and thrombocytopenic purpura. *J Thromb Haemost.* 2003; 1:2038-2040; discussion 2040-2035).

It is believed that the presence of hyper-reactive UL-vWF multimers in the plasma due to ADAMTS13 deficiency could be associated with an increased risk of arterial thrombosis linked to coronary heart disease.

Therefore, a strong need exists for providing new compositions which are capable of preventing and/or treating thrombi caused by certain disorders in a patient.

BRIEF SUMMARY OF THE INVENTION

An object of the present invention is to provide a pharmaceutical composition having thrombolytic activity. The pharmaceutical composition comprises a pharmaceutically effective amount of ADAMTS13 or a biologically active derivative thereof, and optionally one or more pharmaceutically acceptable carrier and/or diluent. Said composition may also comprise one or more additional active ingredient. Further, the present invention relates to a method of treating or preventing a disorder associated with the formation and/or presence of one or more thrombus and to a method of disintegrating one or more thrombus in a patient in need thereof. Examples of disorders associated with the formation and/or the presence of one or more thrombus are hereditary thrombotic thrombocytopenic purpura (TTP), acquired TTP, arterial thrombosis, acute myocardial infarction (AMI), stroke, sepsis, and disseminated intravascular coagulation (DIC). Accordingly, a pharmaceutically effective amount of ADAMTS13 or a biologically active derivative thereof can be used for the preparation of a pharmaceutical composition for treating or preventing a disorder associated with the formation and/or the presence of one or more thrombus and for disintegrating one or more thrombus in a patient in need thereof. Said pharmaceutically effective amount of ADAMTS13 or a biologically active derivative thereof may range, for example, from 0.1 to 20 mg/kg body weight.

BRIEF DESCRIPTION OF THE DRAWINGS

FIG. 9. Table 1: Hemodynamic parameters prior to and after application of A23187 on venules (FIG. 1); Table 2: Hemodynamic parameters prior to and after application of ferric chloride on arterioles (FIG. 5).

DETAILED DESCRIPTION OF THE INVENTION

Figure 1:
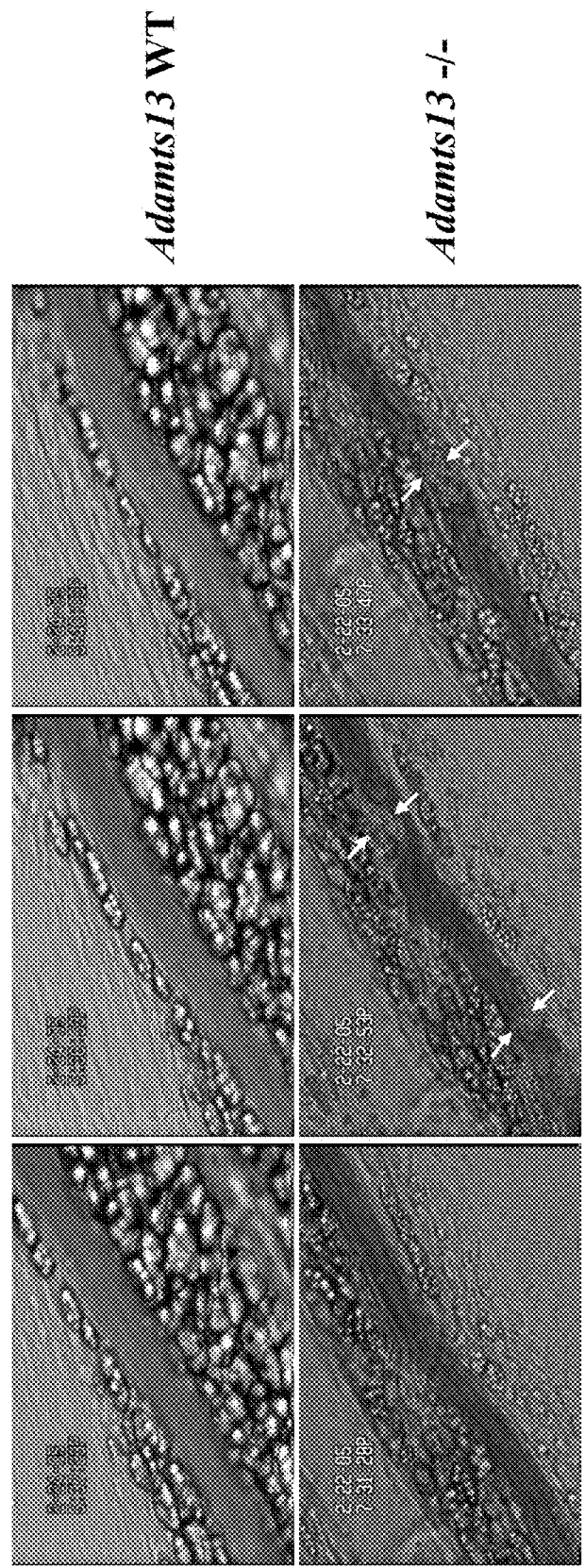
FIG. 1. Thrombus formation in microvenules. Mesenteric venules of approx. 25-30 μm in diameter were visualized after an incision was made through the abdominal wall to expose the mesentery of live mice. One min after topical superfusion of A23187, thrombus formation was observed in Adamts13 −/−mice (n=5). The arrows indicate the microthrombi. No microthrombi formation was observed in WT mice treated identically (n=5). Thus, stimulation of Weibel-Palade body secretion can lead to spontaneous thrombus formation in Adamts13−/− mice in the absence of vascular injury.

One aspect of the present invention relates to a pharmaceutical composition having thrombolytic activity, comprising a pharmaceutically effective amount of ADAMTS13 or a biologically active derivative thereof.

The term "thrombolytic activity" as used herein means the disintegration of one or more thrombus. Suitable methods for the determination of thrombolytic activity are well known in the art. For example, suitable methods are the determination of the lysis of a whole blood clot using tPA or streptokinase, or the determination of the thrombus lysis in vivo.

The term "disintegration" as used herein includes the partial or complete disintegration, dissolving, dissolution, destruction and/or lysis of a thrombus.

The term "thrombus" as used herein comprises a blood clot, especially a platelet-comprising blood clot, a microthrombus, and/or an embolus. Said thrombus may be attached to an arterial or venous blood vessel or not, and may partially or completely block the blood flow in an arterial or venous blood vessel.

The term "biologically active derivative" as used herein means any polypeptides with substantially the same biological function as ADAMTS13. The polypeptide sequences of the biologically active derivatives may comprise deletions, additions and/or substitution of one or more amino acids whose absence, presence and/or substitution, respectively, do not have any substantial negative impact on the biological activity of polypeptide. The biological activity of said polypeptides may be measured, for example, by the reduction or delay of platelet adhesion to the endothelium, the reduction or delay of platelet aggregation, the reduction or delay of the formation of platelet strings, the reduction or delay of thrombus formation, the reduction or delay of thrombus growth, the reduction or delay of vessel occlusion, the proteolytical cleavage of vWF, and/or the disintegration of thrombi.

The terms "ADAMTS13" and "biologically active derivative", respectively, also include polypeptides obtained via recombinant DNA technology. The recombinant ADAMTS13 ("rADAMTS13"), e.g. recombinant human ADAMTS13 ("r-hu-ADAMTS13"), may be produced by any method known in the art. One specific example is disclosed in WO 02/42441 which is incorporated herein by reference with respect to the method of producing recombinant ADAMTS13. This may include any method known in the art for (i) the production of recombinant DNA by genetic engineering, e.g. via reverse transcription of RNA and/or amplification of DNA, (ii) introducing recombinant DNA into prokaryotic or eukaryotic cells by transfection, i.e. via electroporation or microinjection, (iii) cultivating said transformed cells, e.g. in a continuos or batchwise manner, (iv) expressing ADAMTS13, e.g. constitutively or upon induction, and (v) isolating said ADAMTS13, e.g. from the culture medium or by harvesting the transformed cells, in order to (vi) obtain substantially purified recombinant ADAMTS13, e.g. via anion exchange chromatography or affinity chromatography. The term "biologically active derivative" includes also chimeric molecules such as e.g. ADAMTS13 (or a biologically active derivative thereof) in combination with Ig, in order to improve the biological/ pharmacological properties such as e.g. half life of ADAMTS13 in the circulation system of a mammal, particularly human. The Ig could have also the site of binding to an optionally mutated Fc receptor.

The rADAMTS13 can be produced by expression in a suitable prokaryotic or eukaryotic host system characterized by producing a pharmacologically effective ADAMTS13 molecule. Examples of eukaryotic cells are mammalian cells, such as CHO, COS, HEK 293, BHK, SK-Hep, and HepG2. There is no particular limitation to the reagents or conditions used for producing or isolating ADAMTS13 according to the present invention and any system known in the art or commercially available can be employed. In one embodiment of the present invention rADAMTS13 is obtained by methods as described in the state of the art.

A wide variety of vectors can be used for the preparation of the rADAMTS13 and can be selected from eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses, etc., using promoters such as CMV, SV40, EF-1, UbC, RSV, ADV, BPV, and β-actin.

Optionally, the pharmaceutical composition of the present invention also comprises one or more pharmaceutically acceptable carrier and/or diluent.

The pharmaceutical composition of the present invention may also comprise one or more additional active ingredients such as e.g. anti-thrombotic agents, agents that stimulate ADAMTS13 production/secretion by the treated patient/ individual, agents that inhibit the degradation of ADAMTS13 and thus prolonging its half life, agents that enhance ADAMTS13 activity (for example by binding to ADAMTS13, thereby inducing an activating conformational change), or agents that inhibit ADAMTS13 clearance from circulation, thereby increasing its plasma concentration. Examples of anti-thrombotic agents include anti-platelets, t-PA, aspirin and heparin.

The present invention further relates to a method of treating or preventing a disorder associated with the formation and/or the presence of one or more thrombus, comprising the step of administering a composition according to the invention to a patient. Said disorder may be due to hereditary defects, inflammatory diseases, stroke or septic conditions. Examples of disorders associated with the formation and/or the presence of one or more thrombus are hereditary thrombotic thrombocytopenic purpura (TTP), acquired TTP, arterial thrombosis, acute myocardial infarction (AMI), stroke, sepsis, disseminated intravascular coagulation (DIC), and venous thrombosis, such as e.g. deep vein thrombosis or pulmonary embolism.

Another aspect of the present invention relates to a method of disintegrating one or more thrombus in a patient, comprising the step of administering a composition according to the present invention to said patient.

The route of administration of the composition of the present invention does not exhibit a specific limitation and can be, for example, subcutaneous or intravenous. The term "patient" as used in the present invention includes mammals, particularly human.

Furthermore, the present invention relates to the use of a pharmaceutically effective amount of ADAMTS13 or a biologically active derivative thereof for the preparation of a pharmaceutical composition for treating or preventing a disorder associated with the formation and/or the presence of one or more thrombus.

Another aspect of the present invention is the use of a pharmaceutically effective amount of ADAMTS13 or a biologically active derivative thereof for the preparation of a pharmaceutical composition for disintegrating one or more thrombus in a patient in need thereof.

The pharmaceutically effective amount of ADAMTS13 or a biologically active derivative thereof may range, for example, from 0.1 to 20 mg/kg body weight.

The present invention will be further illustrated in the following examples, without any limitation thereto.

EXAMPLES

Example 1: Endothelial Activation Results in Thrombi Formation in Microvenules of Adamts 13 −/− Mice More platelet sticking/translocating in venules (200-250 μm) activated with calcium ionophore A23187 (a secretagouge of Weibel-Palade bodies) at low shear rate (approx. 100 $s^{-1}$) in Adamts13 −/− mice has been observed compared with WT. It was investigated whether activation of microvenule endothelium by A23187 could result in platelet aggregation resulting in thrombus formation. A23187 does not denude the endothelium (Andre P, Denis C V, Ware J, Saffaripour S, Hynes R O, Ruggeri Z M, Wagner D D. Platelets adhere to and translocate on von Willebrand factor presented by endothelium in stimulated veins. Blood. 2000; 96:3322-3328). The shear rate (200-250 $s^{-1}$) and diameter of all the venules (25-30 μm) studied were similar for Adamts13 −/− and WT mice (Table 1). In the microvenules of Adamts13 −/− mice, 45 sec to 1 min after topical superfusion of A23187, platelet aggregation resulted in thrombus formation was observed (FIG. 1). The thrombi were unstable and flushed away in the blood stream leading to frequent embolization causing downstream occlusion. However, the occlusion lasted only 3-4 seconds and the venule reopened afterwards. Thrombus formation was no longer seen at the site of stimulation 2 min after A23187 superfusion. In WT mice treated identically, strings of platelets and very small platelet aggregates could be seen attached to the endothelium for 1 sec, but this did not result in thrombus formation. Arterioles running parallel to the venules in Adamts13 −/− or WT mice did not show any platelet aggregation or thrombus formation. No platelet strings could be observed in the arterioles. These observations demonstrate that ADAMTS13 inhibits platelet aggregation and thus prevents thrombus formation in the microvenules.

Figure 2:
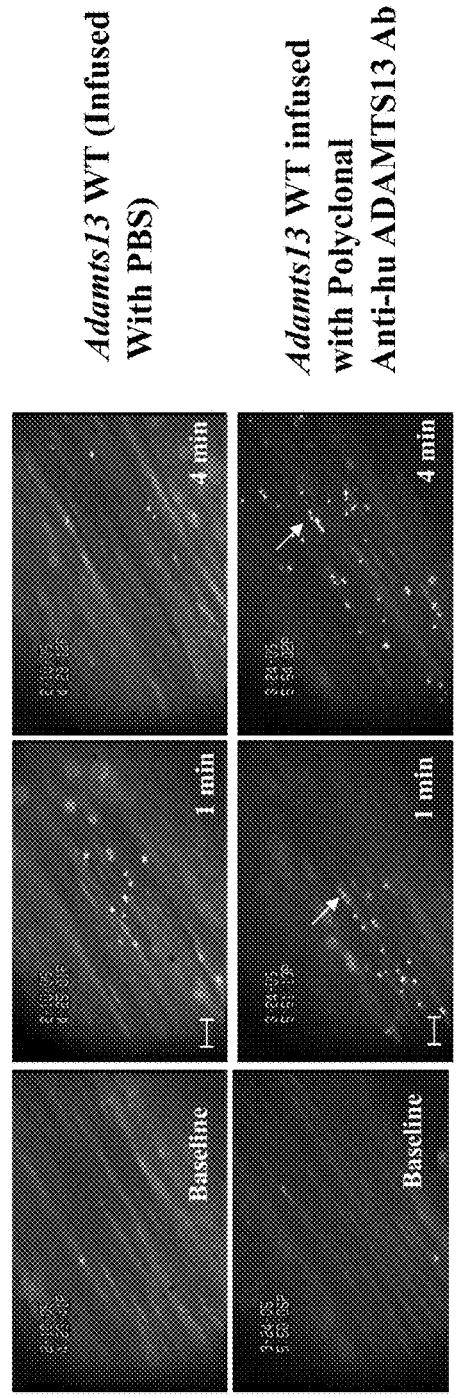
FIG. 2. ADAMTS13 inhibitor increases platelets adhesion and string formation to vessel wall. Fluorescently-labeled platelets representing approx. 2.5% of total platelets were observed in mesenteric venules (200-250 μm) of live mice before (baseline) and after A23187 superfusion. A: Platelets began to adhere to the endothelium 30 to 45 seconds after superfusion. In WT (infused with anti-human ADAMTS13 Ab) mice (n=4) more platelets adhered to vessel wall after 4 min compared to WT (infused with PBS) control (n=4). Arrowheads indicate the 20 μm strings of platelets attached at one end to endothelium and waving in blood stream. Inset time points in lower right corner refer to the time after superfusion of A23187. Bar shown in the middle panel is (approx.) 50 μm. B: In 5 out of 7 WT mice infused with inhibitor to ADAMTS13 an approx. 25-35 μm long platelets string anchored to the vessel wall for up to 10 sec. Inset time points in lower right corner refer to the time after superfusion of A23187. Bar shown in the middle panel is (approx.) 25 μm.
Figure 2:
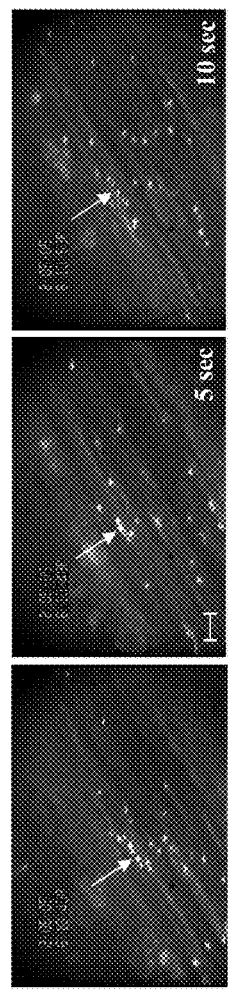

Example 2: An Antibody to ADAMTS13 Induces Formation of Platelets Strings in Venules of WT Mice Previous studies have shown that most patients suffering from the acquired form of TTP have autoimmune inhibitors to ADAMTS13 (Tsai H M, Lian E C. Antibodies to von Willebrand factor-cleaving protease in acute thrombotic thrombocytopenic purpura. *N Engl J. Med.* 1998; 339:1585-1594; Furlan M, Robles R, Galbusera M, Remuzzi G, Kyrle P A, Brenner B, Krause M, Scharrer I, Aumann V, Mittler U, Solenthaler M, Lammle B. von Willebrand factor-cleaving protease in thrombotic thrombocytopenic purpura and the hemolytic-uremic syndrome. *N Engl J Med.* 1998; 339: 1578-1584). Polyclonal anti-human ADAMTS13 Ab (dissolved in PBS) was infused in WT mice 2 hr before the surgery. After topical superfusion of A23187 of both control mice (infused with PBS) and mice infused with Anti-ADAMTS13 Ab, many platelets stuck/translocated on the endothelium, reaching a peak of platelet adhesion between 45 sec to 1 min that progressively decreased with time. However, more platelet sticking was observed 4 min after the A23187 application in the Ab-infused WT as compared with control (FIG. 2A). The phenomenon observed was similar to Adamts13 −/−. Strings of platelets varying from 20-40 μm attached at one end to the endothelium and waving in the blood stream were observed. Strings of platelets were either not seen or were very short lived (less than 2 sec) in the mice injected with PBS or control Ig. In WT mice on a genetic background marked by elevated vWF levels (CASA/Rk), treated with inhibitory antibody, the strings of platelets were even longer (varying from 30-60 μm) indicating that these were formed primarily by vWF polymers. (In some mice, these platelet strings anchored to the endothelium for up to 10 sec (FIG. 2B) and then were washed away.)

Figure 3:
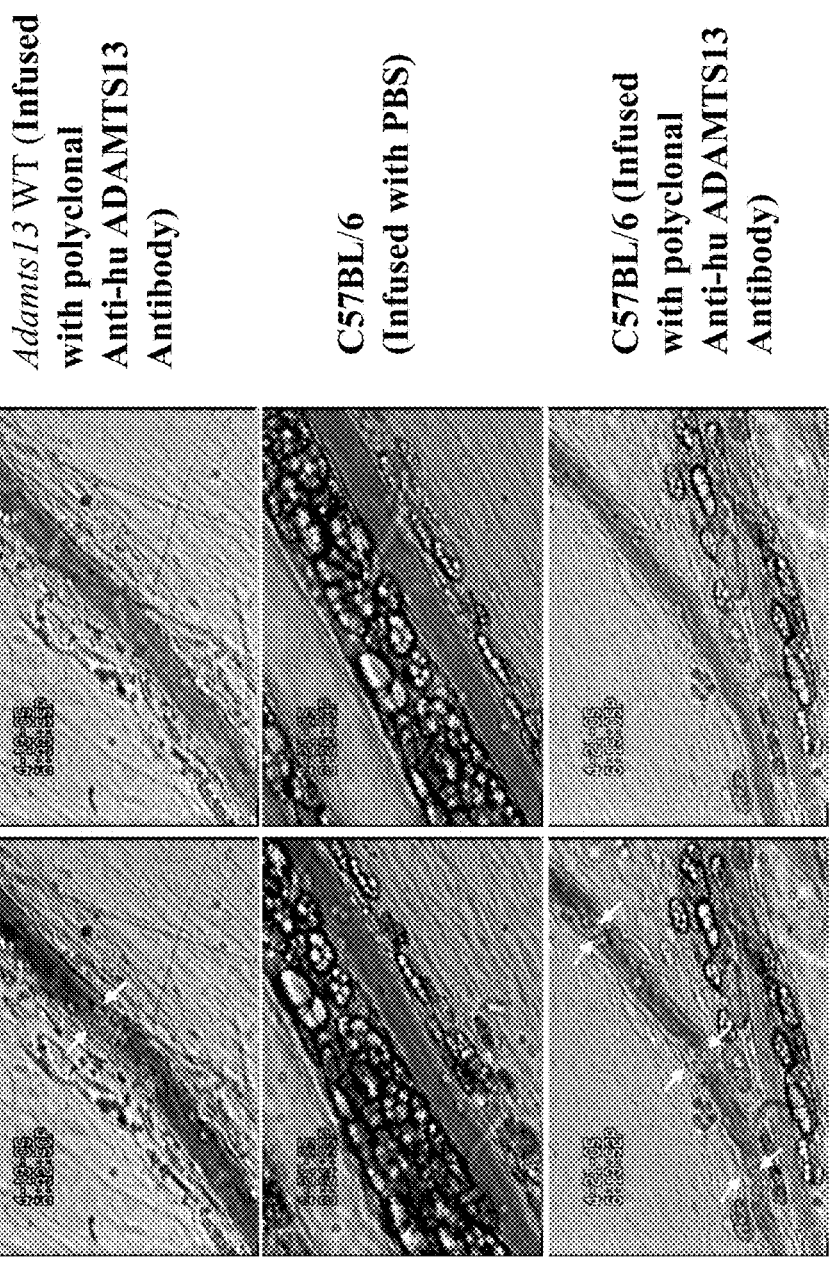
FIG. 3. Thrombus formation in microvenules of WT mice infused with ADAMTS13 Inhibitor. Mesenteric venules of approx 25-30 μm in diameter were observed. One min after topical superfusion with A23187, thrombus formation was observed in 4 out of 6 Adamts13 WT mice infused with ADAMTS13 inhibitor. The microthrombi formation was similar to that seen in Adamts13 −/− mice (FIG. 1). Arrowheads indicate microthrombi. The microthrombi did not form in WT mice infused with PBS (n=5).

Example 3: ADAMTS13 Inhibitor Results in Thrombi Formation in Microvenules in WT Mice In WT mice, infused with anti-human ADAMTS13-Ab 2 hours before surgical preparation, microthrombi formed on the vessel wall 45 sec to 1 min after topical superfusion of A23187 in 4 out of 6 mice (FIG. 3). The microthrombi appearance were similar to those seen in the Adamts13−/− mice (FIG. 1). Then, the inhibitory antibody was infused in the WT mice on a C57BL/6 background. In three out of 5 mice microthrombi formed. In control WT mice, minute platelet aggregates could be seen attached to the endothelium but did not result in thrombus formation (n=3).

Figure 4:
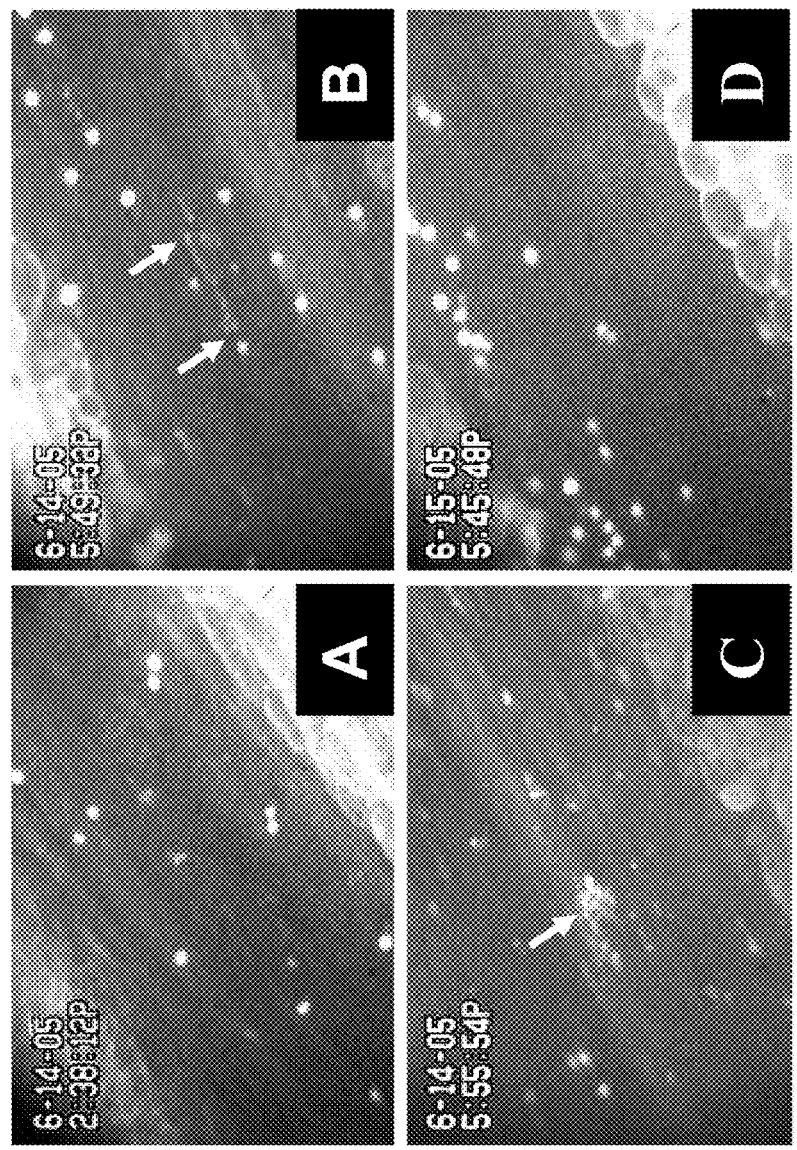
FIG. 4. Recombinant ADAMTS13 inhibits platelet strings in Adamts13 −/− mice. Rhodamin 6G was used to label endogenous platelets and leukocytes. 1 mM histamine (200 μl) was administered i.p. 15 mins before surgery and 3 mesenteric venules of approx. 200-300 μm in diameter were visualized per mouse. A: No platelet strings are seen in Adamts13 WT mice (n=5). B: Platelet strings (indicated by arrowheads) are seen in the Adamts13 −/− mice (n=5). C: The platelet strings could form platelet aggregates in Adamts13 −/− mice as indicated by arrowhead. D: Infusion of recombinant human ADAMTS13 protein inhibits the platelets strings in Adamts13 −/− mice (n=4).

Example 4: Histamine Induces Platelets Strings in the Venules of Adamts13 −/− Mice, Whereas, Recombinant ADAMTS13 Inhibits the Formation Histamine produced during inflammation is a secretagouge of Weibel-Palade bodies and stimulates the endothelium. Endogenous platelets were labeled by infusing Rhodamine 6G i.v. prior to surgery. One mM (200 μl) histamine was injected i.p. 15 min before the surgical preparation in the Adamts13 −/− (n=5) and WT (n=5) mice and venules at a shear rate of approx. 100 $s^{-1}$ were visualized. In the WT, strings of platelets were not seen or were short lived (less than 5 sec, FIG. 4A), whereas in the Adamts13 −/− platelet strings varying from 20-100 μm could be seen (FIG. 4B) anchored to the endothelium for about a minute. In some mice, the platelet strings anchored to the endothelium from 2 to 5 min. Some strings appeared to coalesce forming aggregates (FIG. 4C) that were later released into the blood stream. Infusion of recombinant human ADAMTS13 (r-hu ADAMTS13) protein in the Adamts13 −/− mice (n=4, 3 venules per mouse) inhibited platelet strings in all the 12 venules examined (FIG. 4D), thus demonstrating the activity of ADAMTS13 at low shear.

Figure 5:
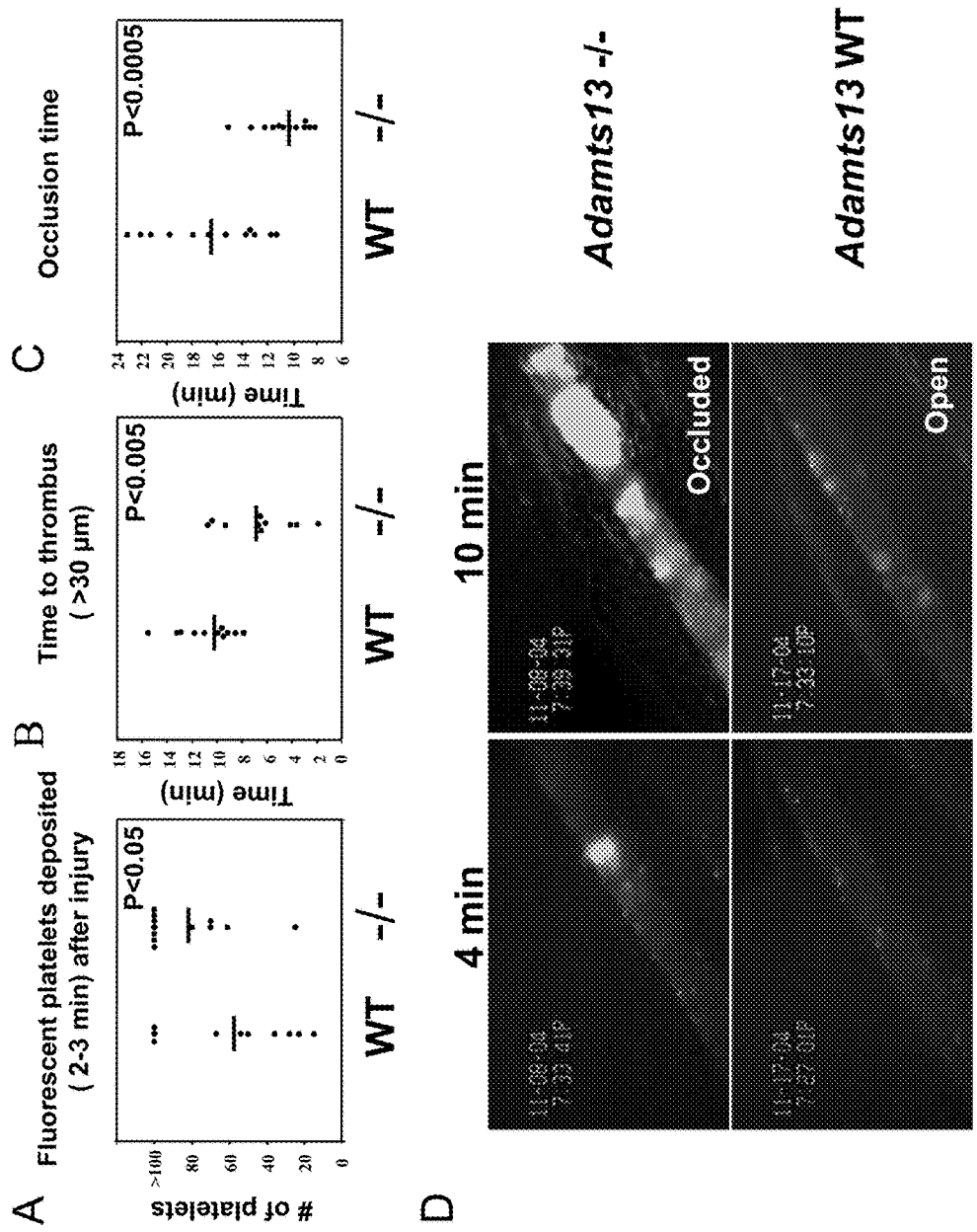
FIG. 5. Quantitative analysis of platelet adhesion and thrombi formation in arterioles of WT and Adamts 13 −/− mice. A: The number of fluorescent platelets deposited per minute was determined in the interval 2-3 min after injury (total number of adherent platelets counted in 1 min interval). For statistics and mean, platelets greater than 100 was considered as 100. Absence of ADAMTS13 in the plasma clearly influences the early platelet interaction with the subendothelium. Compared with WT, in Adamts 13 −/− more platelets were deposited on the vessel wall (P<0.05). B: Thrombus (>30 μm) appeared sooner after injury in Adamts13 −/− mice (mean=6.64±0.93) compared with WT (mean=10.78±0.80) and this was statistically significant (P<0.005). This demonstrates that cleavage of UL-vWF multimers by ADAMTS13 delays thrombus formation. C: The occlusion time when blood flow completely stopped for 10 sec was determined. Both WT and Adamts13 −/− mice occluded at the site of injury; however in Adamts13 −/− mice occlusion time was shorter (mean=10.56±0.72) as compared with WT (mean=16.69±1.25 minutes). The difference was highly statistically significant (P<0.0005). D: Fluorescently-labeled platelets representing approx. 2.5% of total platelets were observed in mesenteric arterioles of live mice after ferric chloride injury. Blood flow was from left to right. Inset time points in lower right corner refer to the time after injury. Single adherent platelets are seen in the arteriole at 4 min after injury in the WT, whereas a thrombus (approx. 30 μm) can already be seen in the Adamts13 −/− mouse arteriole at the same time point. The vessel was occluded at 10 min by a thrombus at the site of injury in Adamts13 −/− mice, while the WT mouse arteriole remained opened at that time. Photographs are representative of 10 mice of each genotype.

Example 5: Platelet Binding to Sub Endothelium is Increased in Adamts13 −/− Mice Ferric chloride ($FeCl_3$) injury leads to deendothelization and exposes sub endothelium (Ni H, Denis C V, Subbarao S, Degen J L, Sato T N, Hynes R O, Wagner D D. Persistence of platelet thrombus formation in arterioles of mice lacking both von Willebrand factor and fibrinogen. *J Clin Invest.* 2000; 106:385-392). Platelet subendothelial interactions after injury at arterial shear are initiated by GPIb-vWF interaction and then propagated by other receptors (Ni H, Denis C V, Subbarao S, Degen J L, Sato T N, Hynes R O, Wagner D D. Persistence of platelet thrombus formation in arterioles of mice lacking both von Willebrand factor and fibrinogen. *J Clin Invest.* 2000; 106:385-392). In both WT and Adamts13 −/− mice, platelet-vessel wall interaction started rapidly after ferric chloride application to the arteriole. The number of animals in which more than 100 platelets were deposited 2-3 min after injury was higher in Adamts13 −/− mice (FIG. 5A). In the Adamts13 −/−, 7 out of 12 mice showed greater than 100 platelets deposited on the vessel wall, compared to 3 of 10 in the WT mice. The results were statistically significant (P<0.05, FIG. 5A).

Example 6: Accelerated Thrombus Formation in Injured Arterioles of Adamts 13 −/− Mice vWF present in the plasma is either constitutively synthesized by endothelial cells or is secreted in the form of unusually large multimers from the platelet α-granules and endothelial Weibel-Palade bodies upon activation. UL-vWF is the most adhesive and reactive form of vWF and may lead to platelet aggregation resulting in a thrombus if not processed by ADAMTS13. In the ferric chloride thrombosis model in the Adamts13 −/− mice, thrombi grew faster as thrombi greater than 30 μm were seen at 6.64±0.93 min compared to 10.78±0.80 min in the WT mice and the results were statistically significant (P<0.005, FIG. 5B). The thrombi grew to occlusive size in 10.56±0.72 min in Adamts13 −/−, whereas in WT still the vessels were open (P<0.0005, FIGS. 5C and 5D). In the WT, the mean vessel occlusion time was 16.69±1.25 after injury (P<0.0005). All the vessels occluded at the site of injury. The shear rate and diameter of arterioles studied were similar for Adamts13 −/− and WT mice (Table 2). Of note, in arterioles of Adamts13 −/− mice the mean time for formation of thrombus (>30 μm) as well as mean occlusion time were less than for any individual WT mouse (FIGS. 5B and 5C). It has been observed that emboli (>30 μm) formed in 4 out of 10 (40%) Adamts13 −/− mice whereas only in 2 of 11 (18.2%) WT mice showed embolization. Thus the Adamts13 −/− thrombi appeared slightly less stable than WT. The observed embolization in Adamts13 −/− mice did not lead to downstream occlusion.

Figure 6:
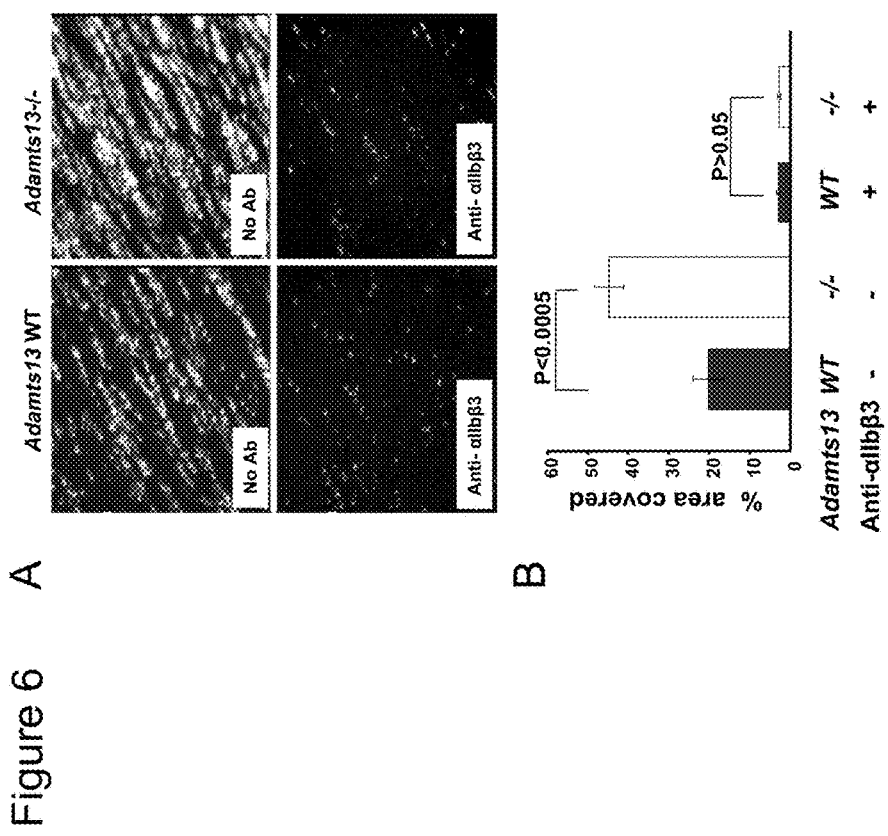
FIG. 6. Inhibition of integrin αIIbβ3 blocks thrombus formation of ADAMTS13−/− platelets on collagen under arterial shear rate conditions. Adamts13 +/+ or Adamts13−/− whole blood was perfused for 2 min over a collagen surface at a shear rate of 1500 s−1. A: Representative images are shown. Upper panels-untreated whole blood, lower panels-pretreated with blocking antibody against αIIbβ3 (JON/A). B: Quantification of the surface area covered by platelets after 2 min of perfusion. Four frames from different areas of the flow chamber were analyzed for each blood sample. Data represent the mean percentage of surface area covered by fluorescent platelets±SEM (n=3-4).

Example 7: ADAMTS13-Deficiency Enhances Thrombus Growth in a αIIbβ3 Integrin-Dependent Manner In vitro flow chamber studies were performed with whole blood in the presence or absence of a blocking antibody (JON/A) against αIIbβ3 (Bergmeier W, Schulte V, Brockhoff G, Bier U, Zirngibl H, Nieswandt B. Flow cytometric detection of activated mouse integrin alphaIIbbeta3 with a novel monoclonal antibody. Cytometry 2002; 48:80-86) (FIG. 6). To quantify the size of the thrombi, the surface area covered by fluorescently-labeled platelets was determined. Adamts13 −/− blood formed significantly larger thrombi than WT when perfused over collagen for 2 minutes at a shear rate of 1500 s$^{-1}$ (44.66±3.63% vs. 20.22±3.88%, P<0.0005), demonstrating again the key role of ADAMTS13 in limiting thrombus growth. In the presence of the blocking antibody to αIIbβ3, only single platelets adhered to the collagen surface and thrombus formation was completely inhibited in both the WT and Adamts13−/− blood (3.01±0.97% vs. 2.82±0.39%, P>0.05). In addition, it was tested whether infusion of ADAMTS13 inhibitory antibody into beta3 integrin-deficient mice (Hodivala-Dilke K M, McHugh K P, Tsakiris D A, Rayburn H, Crowley D, Ullman-Cullere M, Ross F P, Coller B S, Teitelbaum S, Hynes R O. Beta3-integrin-deficient mice are a model for Glanzmann thrombasthenia showing placental defects and reduced survival J Clin Invest 1999; 103:229-238) would induce thrombus formation after ferric chloride injury. In injured arterioles of beta3 −/− mice (3 animals were evaluated) no thrombi could be detected despite the presence of the anti-ADAMTS13 antibody (not shown). Taken together these results indicate that, at the arterial shear rates, ultralarge vWF enhances thrombus growth in a αIIbβ3-dependent manner.

Figure 7:
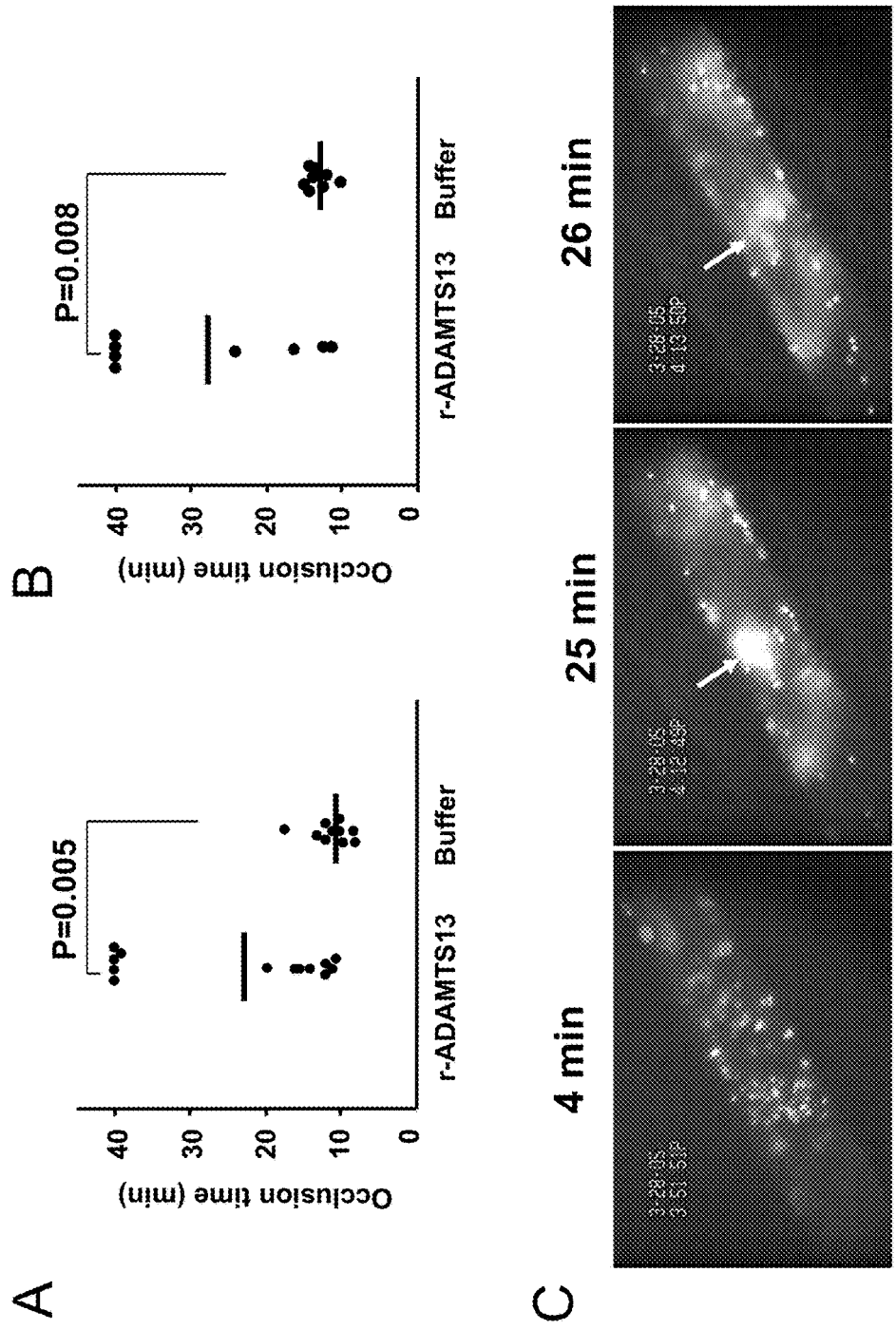
FIG. 7. Infusion of recombinant human ADAMTS13 inhibits thrombus growth. Recombinant human ADAMTS13 was infused (i.v.) in the Adamts13 −/− mice 15 min before the ferric chloride injury. The occlusion time (blood flow completely stopped for 10 sec) was determined. A: Five out of 13 Adamts13 −/− mice, infused with recombinant human ADAMTS13 did not occlude in the arteriole at up to 40 min of observation time (mean occlusion time=23.80±3.71 min), whereas, all 10 Adamts13−/− mice infused with recombinant buffer only occluded (mean occlusion time=11.17±0.87); (P=0.005). B: Occlusion time in injured arterioles of WT (C57Bl/6J) mice infused either with r-hu ADAMTS13 (mean occlusion time=27.99±4.72 min) or buffer alone (mean occlusion time=13.12±0.55 min). C: Representative fluorescent images of injured arteriole of an Adamts13 −/− mouse treated with r-hu ADAMTS13 are shown. Arrowheads indicate a disintegrating thrombus.

Example 8: Infusion of Recombinant Human ADAMTS13 in Adamts13 −/− or WT (C57BL/6J) Mice Inhibits Thrombus Growth by Destabilizing the Platelet Aggregate or Thrombus Cleavage of the vWF subunit into proteolytic fragments by recombinant human ADAMTS13 (r-hu ADAMTS13) has been shown in vitro (Plaimauer B, Zimmermann K, Volkel D, Antoine G, Kerschbaumer R, Jenab P, Furlan M, Gerritsen H, Lammle B, Schwarz H P, Scheiflinger F. Cloning, expression, and functional characterization of the von Willebrand factor-cleaving protease (ADAMTS13). *Blood.* 2002; 100:3626-3632). It has been demonstrated that r-hu ADAMTS13 corrects the vWF cleavage defect in hereditary TTP plasma (Antoine G, Zimmermann K, Plaimauer B, Grillowitzer M, Studt J D, Laemmle B, Scheiflinger F. ADAMTS13 gene defects in two brothers with constitutional thrombotic thrombocytopenic purpura. Br J Haematol 2003; 120:821-824). Since accelerated growth of thrombi in Adamts13−/− mice has been observed, it is hypothesized that ADAMTS13 negatively modulates thrombus growth and therefore infusion of r-hu ADAMTS-13 in Adamts 13 −/− mice could delay thrombus formation. The concentration of the circulating human protein was approximately 8.8 U/ml 17 min after infusion and 1.1 U/ml 53 min after infusion of r-hu ADAMTS13 into Adamts 13 −/− mice. These times correspond approximately to the onset of ferric chloride injury and the termination of the experiment. In 5 out of 13 Adamts13 −/− mice infused with r-hu ADAMTS 13, injured arterioles did not occlude for up to 40 min when the experiment was terminated (FIG. 7A). The effect of the infused r-hu ADAMTS13 was more than that of endogenous ADAMTS13 in WT mice as in this injury model all WT vessels occluded at less than 24 min (FIG. 5C). The mean occlusion time was significantly prolonged in comparison with the control mice infused with buffer (P<0.0005). In all mice whose arterioles did not occlude, thrombi did form but were unstable and disintegrated (FIG. 7C). This phenomenon of thrombi formation and disintegration was present during the entire period of observation. The infusion of r-hu ADAMTS13 prior to injury in WT mice (C57BI/6J) caused significant delay in occlusion time with half of the arterioles not occluding by 40 min while all arterioles of WT mice infused with vehicle occluded by 15 min (FIG. 7 B, P<0.008). Thus, ADAMTS13 appears to have a significant anti-thrombotic potential even in WT mice with normal levels of endogenous ADAMTS13 protein.

Figure 8:
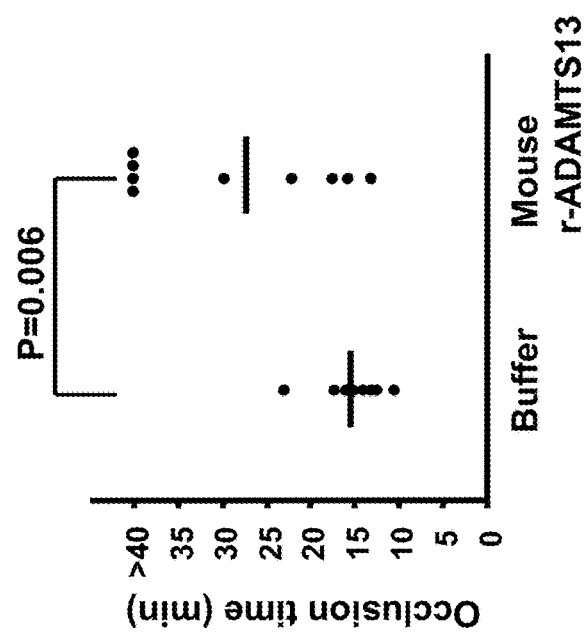
FIG. 8. Infusion of recombinant mouse ADAMTS13 inhibits thrombus growth in WT mice. Recombinant mouse ADAMTS13 (2.6 mg/kg mouse) was infused (i.v.) into the WT mice 5 min before the ferric chloride injury. Four out of nine WT mice infused with recombinant mouse ADAMTS13 did not occlude the injured arterioles at 40 min of observation time (mean occlusion time=27.04±3.84 min), whereas all WT mice infused with buffer occluded (mean occlusion time=15.15±1.18 min, P=0.006).

Example 9: Infusion of Recombinant Mouse ADAMTS13 Inhibits Thrombus Growth in WT Mice r-mouse ADAMTS13 (2.6 mg/kg mouse) was infused (i.v.) into the WT mice 5 min before the ferric chloride injury. A previously described model was used with slight modifications as described below. FIG. 8 shows that four out of nine WT mice infused with r-ADAMTS13 did not occlude the injured arterioles at 40 min of observation time (mean occlusion time=27.04±3.84 min), whereas all WT mice infused with buffer occluded (mean occlusion time=15.15±1.18 min, P=0.006). Western analysis of the plasma samples taken at the end of the experiment showed that the shorter occlusion time in some of the mice infused with r-ADAMTS13 (similar to WT) was due to increased clearance of the recombinant protein. Thus, mouse ADAMTS13 appears to have the same anti-thrombotic potential as the human ADAMTS13 in WT mice with normal levels of endogenous ADAMTS protein.

These results show that ADAMTS13 has an antithrombotic as well as thrombolytic activity.

Experimental Procedures

Animals

Mice used in the examples were siblings obtained from crosses of Adamts13+/− mice on C57BL/6J/129Sv background (Motto D G, Chauhan A K, Zhu G, Homeister J, Lamb C B, Desch K C, Zhang W, Tsai H M, Wagner D D, Ginsburg D. Shigatoxin triggers thrombotic thrombocytopenic purpura in genetically susceptible ADAMTS13-deficient mice. *J Clin Invest* 2005; 115:2752-2761). The mice of pure C57Bl/6J background were purchased from the Jackson Laboratory, Bar Harbor, Me. and beta3 integrin−/− mice on Balb/C background were a gift from Richard Hynes (MIT). The mice used for intravital microscopy were young mice (approx. 4 weeks old), both male and female, weighing 14 to 18 grams. Infused platelets were isolated from 4 to 6 months old mice of the same genotype. Animals were bred and housed at CBR Institute for Biomedical Research and all experimental procedures were approved by its Animal Care and Use Committee.

Materials

Calcium ionophore A23187 and ferric chloride were from Sigma Chemicals, St. Louis, Mo.

Blood Sampling and Platelet Preparation

Blood was harvested from the retro-orbital venous plexus by puncture and collected in 1.5 ml polypropylene tubes comprising 300 µl of heparin (30 U/ml). Platelet rich plasma (PRP) was obtained by centrifugation at 1200 rpm for 5 min. The plasma and buffy coat comprising some RBCs were gently transferred to fresh polypropylene tubes and recentrifuged at 1200 rpm for 5 min. The PRP was transferred to fresh tubes comprising 2 µl of $PGI_2$ (2 µg/ml) and incubated at 37° C. for 5 min. After centrifugation at 2800 rpm, pellets were resuspended in 1 ml modified Tyrode's-HEPES buffer (137 mM NaCl, 0.3 mM $Na_2HPO_4$, 2 mM KCl, 12 mM $NaHCO_3$, 5 mM HEPES, 5 mM glucose, 0.35% BSA) comprising 2 µl of $PGI_2$ and incubated at 37° C. for 5 min. The suspended pellet was centrifuged at 2800 rpm for 5 min. In order to remove $PGI_2$, the washing step was repeated twice and platelets were fluorescently labeled with calcein AM 0.25 mg/mL (Molecular Probes, Eugene, Oreg.) for 10 min at room temperature.

Polyclonal Anti-ADAMTS13 IgG Production and Purification

Polyclonal rabbit anti-human ADAMTS13 IgG was produced by Baxter Bioscience, Vienna Austria. The antibody was obtained by immunization of New Zealand white rabbits with purified r-hu ADAMTS13, C-terminally tagged with six His residues. Two rabbits were immunized by injection of 20 µg of r-hu ADAMTS13 (6-His) in 200 µl of complete Freund's adjuvant. The animals were boostered after two, four and six weeks by injecting 20 µg of r-hu ADAMTS13 (6-His) in 200 µl of incomplete Freund's adjuvant. After eight weeks the rabbits were sacrificed and bled. IgG antibodies were purified by Protein G affinity chromatography (HiTrap Protein G HP column; Amersham Bioscience, Piscataway, N.J., USA) and formulated in PBS.

Thrombosis in Microvenules

Intravital microscopy was as done as described in Frenette P S, Johnson R C, Hynes R O, Wagner D D. Platelets roll on stimulated endothelium in vivo: an interaction mediated by endothelial P-selectin. *Proc Natl Acad Sci USA*. 1995; 92:7450-7454. Briefly, mice were anesthetized with 2.5% tribromoethanol (0.15 ml/10 g) and an incision was made through the abdominal wall to expose the mesentery and mesenteric venule of 25 to 30-µm diameter was studied. Exposed mesentery was kept moist by periodic superfusion using PBS (without $Ca^{2+}$ or $Mg^{2+}$) warmed to 37° C. The mesentery was transluminated with a 12 V, 100 W, DC-stabilized source. The shear rate was calculated using an optical Doppler velocity meter as described in Frenette P S, Moyna C, Hartwell D W, Lowe J B, Hynes R O, Wagner D D. Platelet-endothelial interactions in inflamed mesenteric venules. *Blood*. 1998; 91:1318-1324. Venule was visualized using a Zeiss (Germany) Axiovert 135 inverted microscope (Objective 10× and 32×) connected to an SVHS video recorder (AG-6730; Panasonic, Tokyo, Japan). One venule was chosen per mouse and filmed for 3 min for the baseline before the A23187 superfusion (30 µl of a 10 Mmol/L solution) and monitored for 10 min.

Platelet Adhesion in Large Venules

Intravital microscopy was done as described above except mesenteric venules of 200 to 300-µm diameters were studied. Fluorescent platelets ($1.25 \times 10^9$ platelets/kg) were infused through the tail vein. One venule per animal was filmed for 3 minutes for the baseline before the A23187 superfusion (30 µl of a 10 µmol/L solution) and filming continued until after the platelet sticking and rolling returned to baseline. Purified rabbit polyclonal anti-human ADAMTS13 antibody (5 mg/kg mouse) was dissolved in PBS. Control rabbit IgG (Sigma, St. Louis, Mo.) was in PBS. 200 µl of 1 mM histamine (Sigma) was injected i.p. to stimulate the endothelium. 100 µl (0.2 mg/ml) of Rhodamine 6G (Sigma) was injected i.v. to label the endogenous platelets and leukocytes prior to surgery and imaging.

Thrombosis in Arterioles

A model described in Ni H, Denis C V, Subbarao S, Degen J L, Sato T N, Hynes R O, Wagner D D. Persistence of platelet thrombus formation in arterioles of mice lacking both von Willebrand factor and fibrinogen. *J Clin Invest*. 2000; 106:385-392, was used with slight modifications (Ni H, Denis C V, Subbarao S, Degen J L, Sato T N, Hynes R O, Wagner D D. Persistence of platelet thrombus formation in arterioles of mice lacking both von Willebrand factor and fibrinogen. *J Clin Invest*. 2000; 106:385-392). Briefly, mice were anesthetized with 2.5% tribromoethanol (0.15 ml/10 g) and fluorescent platelets ($1.25 \times 10^9$ platelets/kg) were infused through the retro-orbital plexus of the eye. An incision was made through the abdominal wall to expose the mesentery and arterioles of approx. 100 µm diameters were studied. Exposed mesentery was kept moist by periodic superfusion using PBS (without $Ca^{2+}$ or $Mg^{2+}$) warmed to 37° C. The mesentery was transluminated and the shear rate was calculated as described above. Arterioles were visualized using the same microscope described above, equipped with a 100-W HBO fluorescent lamp source (Optic Quip, Highland Mills, N.Y.) with a narrow band fluorescein isothiocyanate filter set (Chroma Technology, Brattleboro, Vt.) and a silicon-intensified tube camera C2400 (Hamamatsu, Tokyo, Japan). Whatman paper saturated with ferric chloride (10%) solution was applied topically which induced vessel injury and denudation of the endothelium. The paper was removed after 5 min and vessel was monitored for 40 min after injury or until occlusion. One arteriole was chosen per mouse.

Quantitative Analysis of Arteriolar Thrombus

Analysis of the recorded tape was performed blinded to the genotype. The parameters that were applied to describe the characteristics of thrombus formation were: (1) Single platelet-vessel wall interaction within 2-3 min, determined as the number of fluorescent platelets that deposited on the 250 µm vessel wall (seen on the video monitor) during 1 min. (2) The time required for formation of a thrombus larger than 30 µm. (3) Thrombus stability by determining the number of thrombi of diameter larger than 30 µm embolizing away from the viewing field before vessel occlusion. (4) Occlusion time of the vessel, that is, time required for blood to stop flowing for 10 sec and (5) site of vessel occlusion, that is, at the site of injury or downstream.

Recombinant Human ADAMTS13 Infusion

Recombinant human ADAMTS13 has been obtained by the methods as described in Plaimauer B, Zimmermann K, Völkel D, Antoine G, Kerschbaumer R, Jenab P, Furlan M, Gerritsen H, Lämmle B, Schwarz H P, and Scheiflinger F. Cloning, expression, and functional characterization of the von Willebrand factor-cleaving protease (ADAMTS13). *Blood* 2002; 100(10):3626-3632. Recombinant human ADAMTS13 protein was dissolved in 150 mmol NaCl/20 mmol Histidin/2% Sucrose/0.05% Crillet 4HP (Tween 80), pH 7.4 (Baxter Bioscience, Vienna, Austria). Recombinant human ADAMTS13 was injected i.v. (3460 U/kg mouse). Levels of human ADAMTS13 antigen were determined by a slight modification of the ELISA method described by Rieger (Rieger M, Kremer Hovinga J A, Konetschny C, Herzog A, Koller L, Weber A, Remuzzi G, Dockal M, Plaimauer B and Scheiflinger F. Relation between ADAMTS13 Activity and ADAMTS13 Antigen Levels in Healthy Donors and Patients with Thrombotic Microangiopathies (TMA). *Thrombosis and Hemostasis* 2006; 95(2): 212-20) and r-hu ADAMTS13 activity was determined according to Gerritsen (Gerritsen H E, Turecek P L, Schwarz H P, Laemmle B, and Furlan M. Assay of von Willebrand factor (vWF)-cleaving protease based on decreased collagen binding affinity of degraded vWF: a tool for the diagnosis of thrombotic thrombocytopenic purpura (TTP). *Thromb Haemost* 1999; 82:1386-1389). 1 U corresponds to the level of ADAMTS13 activity in pooled normal human plasma.

Recombinant Mouse ADAMTS13 Infusion

Recombinant mouse ADAMTS13 has been obtained by the methods as described in Bruno K, Völkel D, Plaimauer B, Antoine G, Pable S, Motto D G, Lemmerhirt H L, Dorner F, Zimmermann K, and Scheiflinger F. Cloning, expression and functional characterization of the full-length murine ADAMTS-13. *J Thromb Haemost* 2005; 3(5):1064-1073. Recombinant mouse ADAMTS13 protein was dissolved in 150 mmol NaCl/20 mmol Histidin/2% Sucrose/0.05% Crillet 4HP (Tween 80), pH 7.4 (Baxter Bioscience, Vienna, Austria).

Flow Chamber Studies

Flow chamber studies were performed as described in Bergmeier (Bergmeier W, Burger P C, Piffath C L, Hoffmeister K M, Hartwig J H, Nieswandt B, and Wagner D D. Metalloproteinase inhibitors improve the recovery and hemostatic function of in vitro-aged or -injured mouse platelets. *Blood* 2003; 102:4229-4235). Briefly, platelets were isolated from heparinized whole blood, washed in modified Tyrode-HEPES buffer, and labeled with 2.5 µg/mL calcein. Platelet poor whole blood was reconstituted with labeled platelets before perfusion in a parallel-plate flow chamber system coated with 100 µg/mL collagen Horm (NYCOMED, Munich, Germany) for 1 h at RT. Where indicated, samples were pretreated with 30 µg/ml JON/A (emfret Analytics, Wuerzburg, Germany) for 10 min prior to perfusion. Platelet adhesion was visualized with an Axiovert 135 inverted microscope (Zeiss). The percentage of surface area covered by fluorescent platelets was analyzed using NIH Image 1.61 software by an individual blinded to genotypes.

Statistical Analysis

Results are reported as the mean±SEM. The statistical significance of the difference between means was assessed by the Student's t test.

Discussion of the Experimental Results

The experimental results have defined a key role for ADAMTS13 in preventing thrombi formation in activated microvenules and excessive thrombus formation in the injured arterioles of mice. Using intravital microscopy, it is shown in vivo in ADAMTS13 −/− mice that activating venules (25-30 µm) results in platelet aggregation leading to microthrombi formation (FIG. 1). Microthrombi do not form in the venules of WT mice treated identically. When released from the activated endothelium, these microthrombi can travel downstream and cause occlusion elsewhere in the small capillaries where they cannot pass, thus leading to organ ischemia. Patients suffering from TTP often have microthrombi that are formed in the microvasculature of organs: like brain, heart, pancreas, spleen, kidney and mesentery. Various agents including viruses, bacterial shiga toxins, drugs such as ticlopidine and clopidogrel, antibodies and immune complexes can trigger vascular activation perhaps inducing Weibel-Palade body release. In arterioles (which have higher shear stress) treated identically with A23187 no thrombi could be seen. This is because either Weibel-Palade bodies were not released in these vessels or, more likely, vWF is washed too quickly from the endothelial surface to promote platelet adhesion.

Autoantibodies neutralizing human ADAMTS13 are a major cause of the acquired type of TTP. Infusion of anti-ADAMTS13 antibody in the WT mice resulted in prolonged adhesion of platelets to secreted vWF and platelet string formation on the stimulated endothelium (FIG. 2A) that was similar to that seen in the Adamts13 −/− mice. The strings of platelets, varying from approx. 20-70 µm in length, can be seen anchored to the endothelium (FIG. 2B). Platelet strings and aggregates were frequently seen in the Adamts13 −/− mice when challenged with Weibel-Palade body secretagogues such as histamine, inflammatory cytokine TNF-α and activated platelets. Infusion of the r-hu ADAMTS13 protein in the Adamts13 −/− mice challenged with histamine inhibits the platelet strings formation. These strings are cleaved at the upstream end.

Activation of microvenules (25 to 30 µm) with A23187 results in platelet aggregates leading to thrombi formation in the Adamts13 WT mice infused with anti-ADAMTS13-Ab (FIG. 3). However, these thrombi embolized rapidly, similar to those in the Adamts13 −/− mice. Microthrombi formation can be also induced in the WT mice on a C57BL/6 background infused with inhibitory antibody. Thus the mouse infused with anti-ADAMTS13 Ab is in many aspects a good model for acquired TTP. In addition, it demonstrates the role of the ADAMTS13 in preventing platelet aggregation in the circulation.

vWF through its receptors, GPIbα and αIIbβ3, contributes to platelet function in initiating platelet aggregation and progression of thrombus formation. The experimental observations that platelet-endothelial interactions are prolonged and that the endothelial activation results in microthrombi in the Adamts13 −/− mice led to the hypothesis that ADAMTS13 deficiency might accelerate thrombus formation in injured arterioles. Indeed, the absence of ADAMTS13 promoted all aspects of thrombus growth. Unexpectedly, even more platelets deposited on the denuded vessel wall after 2-3 mins of injury in the Adamts13 −/− mice as compared with WT (FIG. 5A). Since early platelet deposition in arterioles is vWF dependent, it means that either plasma ADAMTS13 reduces vWF incorporation into the basement membrane when it is exposed to blood, or that it digests vWF already present in the extra-cellular matrix. The rapid thrombus growth and occlusion in Adamts13 −/− mice indicates that ADAMTS13 might cleave vWF multimers incorporated in the thrombus.

It has been suggested that cleavage of VWF domain A2 by ADAMTS13 is facilitated by the binding of VWF to GPIbα. Thus, the VWF-GPIb interaction within the thrombus may negatively regulate thrombus growth. Thrombus formation under venous and arterial flow conditions also depends on major integrin αIIbβ3. The present examples at arteriolar shear rates show that ADAMTS13 modulates the growing thrombus only when platelets in the thrombus express an active beta3 integrin. Under these in vitro and in vivo experimental conditions, ADAMTS13-deficiency did not promote thrombus growth if the major platelet integrin was absent or inhibited (FIG. 6).

In order to inhibit the fast thrombus growth seen in the ADAMTS13 −/− mice, r-hu ADAMTS13 was infused into Adamts13 −/− and WT mice prior to injury. The anti-thrombotic effect of the r-hu ADAMTS13, although highly statistically significant, varied among the animals (FIGS. 7A and 7B). Some mice did not respond to r-hu ADAMTS13 treatment. It is possible that in these mice r-hu ADAMTS13 was proteolytically inactivated by thrombin and plasmin produced at the sites of vascular injury. IL-6 and high amounts of vWF released after inflammation or injury could also reduce ADAMTS13 activity. In the vessels which did not occlude, the phenomenon of thrombi disintegrating and reforming is observed (FIG. 7C). These findings show that ADAMTS13 have both anti-thrombotic and thrombolytic activity. A possible mechanism is ADAMTS13 cleaving the UL-vWF multimers into smaller fragments that are less adhesive or directly cleaving the vWF molecules bridging platelets in a thrombus as is the case in cleavage of platelets attached to strings. In vivo, ADAMTS13 is active at both low venous and high arterial shear stress conditions. It cleaves platelet strings and regulates platelet interaction with the "activated" vessel wall in the venules, prevents thrombi in activated microvenules and modulates the thrombotic response in injured arterioles.

Congenital TTP patients are currently treated by plasma exchange, whereas acquired TTP patients are subjected to plasmapheresis where autoantibodies are removed from the plasma. The antithrombotic and thrombolytic effect of ADAMTS13 protein indicates that besides TTP, e.g. recombinant ADAMTS13 can be used to treat patients suffering with thrombotic disorders due to hereditary defects, inflammatory disease, septic conditions, or venous thrombosis, such as e.g. deep vein thrombosis or pulmonary embolism. The thrombolytic activity of the ADAMTS13 shows that this protein can be used in combination with other therapies to disintegrate thrombi in clogged arteries or after minor stroke.

In summary, the experimental data show that the metalloprotease ADAMTS13 negatively regulates thrombosis, which indicates that the molecule has anti-thrombic activity. Thus, e.g., recombinant human ADAMTS13 protein having thrombolytic activity can be used as a therapeutic agent to treat thrombotic disorders.

It is understood that the examples and embodiments described herein are for illustrative purposes only and that various modifications and changes in light thereof will be suggested to persons skilled in the art and are to be included within the purview of this application and are considered to be within the scope of the appended claims. All publications, patents, and patent applications cited herein are hereby incorporated by reference in their entirety for all purposes.

What is claimed is:

1. A method of treating or preventing deep vein thrombosis in a patient, the method comprising administering a pharmaceutical composition having thrombolytic activity and anti-thrombotic activity intravenously to the patient, wherein the pharmaceutical composition comprises a pharmaceutically effective amount of ADAMTS13 as an active ingredient.

2. The method of claim 1, wherein ADAMTS13 is recombinant human ADAMTS13.

3. The method of claim 1, further comprising administering one or more additional active ingredients.

4. The method of claim 3, wherein the additional active ingredient is selected from the group consisting of an anti-thrombotic agent, an agent that stimulates ADAMTS13 production or secretion, an agent that inhibits ADAMTS13 degradation, an agent that enhances ADAMTS13 activity, and an agent that inhibits ADAMTS13 clearance from circulation.

5. The method of claim 4, wherein the anti-thrombotic agent is selected from the group consisting of anti-platelets, t-PA, aspirin and heparin.

6. The method of claim 1, wherein the pharmaceutically effective amount of ADAMTS13 or a biologically active derivative of ADAMTS13 ranges is from 0.1 to 20 mg/kg weight.

7. The method of claim 1, wherein the patient is a human patient.

8. A method of treating or preventing deep vein thrombosis in a patient, the method comprising administering a pharmaceutical composition having thrombolytic activity and anti-thrombotic activity intravenously to the patient, wherein the pharmaceutical composition comprises a pharmaceutically effective amount of a chimeric molecule comprising ADAMTS13 and Ig.

9. The method of claim 8, wherein ADAMTS13 is recombinant human ADAMTS13.

10. The method of claim 8, further comprising administering one or more additional active ingredients.

11. The method of claim 10, wherein the additional active ingredient is selected from the group consisting of an anti-thrombotic agent, an agent that stimulates ADAMTS13 production or secretion, an agent that inhibits ADAMTS13 degradation, an agent that enhances ADAMTS13 activity, and an agent that inhibits ADAMTS13 clearance from circulation.

12. The method of claim 11, wherein the anti-thrombotic agent is selected from the group consisting of anti-platelets, t-PA, aspirin and heparin.

13. The method of claim 8, wherein the pharmaceutically effective amount of the chimeric molecule is from 0.1 to 20 mg/kg weight.

14. The method of claim 8, wherein the patient is a human patient.

* * * * *